US009606002B2

(12) United States Patent
Bird et al.

(10) Patent No.: US 9,606,002 B2
(45) Date of Patent: Mar. 28, 2017

(54) SPECTRAL IMAGING OF A SAMPLE USING A PLURALITY OF DISCRETE MID-INFRARED WAVELENGTHS

(71) Applicant: Daylight Solutions Inc., San Diego, CA (US)

(72) Inventors: Benjamin Bird, Roslindale, MA (US); Miles James Weida, Poway, CA (US); Jeremy Rowlette, Redwood City, CA (US)

(73) Assignee: DAYLIGHT SOLUTIONS, INC., San Diego, CA (US)

( * ) Notice: Subject to any disclaimer, the term of this patent is extended or adjusted under 35 U.S.C. 154(b) by 0 days.

(21) Appl. No.: 14/796,858

(22) Filed: Jul. 10, 2015

(65) Prior Publication Data

US 2015/0323384 A1    Nov. 12, 2015

Related U.S. Application Data

(63) Continuation-in-part of application No. PCT/US2015/011884, filed on Jan. 18, 2015.
(Continued)

(51) Int. Cl.
*G01J 3/28* (2006.01)
*G01J 3/10* (2006.01)
(Continued)

(52) U.S. Cl.
CPC .............. *G01J 3/10* (2013.01); *G01J 3/108* (2013.01); *G01J 3/28* (2013.01); *G01J 3/2823* (2013.01);
(Continued)

(58) Field of Classification Search
CPC .... G01J 3/108; G01J 5/52; G01J 3/433; G01J 3/2823; G01J 2003/104; G01J 2003/2826; G01J 2003/4332
(Continued)

(56) References Cited

U.S. PATENT DOCUMENTS 8,780,347 B2    7/2014  Kotidis et al.
2003/0117620 A1  6/2003  Balas et al.
(Continued)

FOREIGN PATENT DOCUMENTS

WO    WO2013063316 A1    5/2013
WO    WO2014209471 A2   12/2014
WO    WO2015109274 A1    7/2015

OTHER PUBLICATIONS

Giuseppe Bellisola et al, "Infrared spectroscopy and microscopy in cancer research and diagnosis", American Journal of American Cancer, vol. 2, No. 1, Jan. 1, 2012, pp. 1-21, XP055216511, section 2.; figures 1b, 2, 3; table 1.
(Continued)

*Primary Examiner* — David Porta
*Assistant Examiner* — Gisselle Gutierrez
(74) *Attorney, Agent, or Firm* — Roeder & Broder LLP; Steven G. Roeder

(57) ABSTRACT

Spectrally analyzing an unknown sample (10A) includes (i) providing a spatially homogeneous region (10B) of the unknown sample (10A); (ii) directing a plurality of interrogation beams (16) at the spatially homogeneous region (10B) with a laser source (14), (iii) acquiring a separate output image (245) while the unknown sample (10A) is illuminated by each of the interrogation beams (16) with an image sensor (26A); and (iv) analyzing less than fifty output images (245) to analyze whether a characteristic is present in the unknown sample (10A) with a control system (28) that includes a processor. Each of the interrogation beams (16) is nominally monochromatic and has a different interrogation wavelength that is in the mid-infrared spectral range.

7 Claims, 14 Drawing Sheets

Related U.S. Application Data

(60) Provisional application No. 62/023,099, filed on Jul. 10, 2014, provisional application No. 61/929,050, filed on Jan. 18, 2014.

(51) Int. Cl.
*G01J 5/52* (2006.01)
*G01J 3/433* (2006.01)
*G01J 3/42* (2006.01)
*G01N 21/3563* (2014.01)
*G01N 21/39* (2006.01)

(52) U.S. Cl.
CPC ............... *G01J 3/42* (2013.01); *G01J 3/433* (2013.01); *G01J 5/52* (2013.01); *G01N 21/3563* (2013.01); *G01N 21/39* (2013.01); *G01J 2003/104* (2013.01); *G01J 2003/2826* (2013.01); *G01J 2003/4332* (2013.01)

(58) Field of Classification Search
USPC .................................................. 250/339.06
See application file for complete search history.

(56) References Cited

U.S. PATENT DOCUMENTS

| | | |
|---|---|---|
| 2008/0269616 A1 | 10/2008 | Bloom et al. |
| 2011/0080581 A1 | 4/2011 | Bhargava et al. |
| 2012/0033220 A1 | 2/2012 | Kotidis et al. |
| 2013/0292571 A1 | 11/2013 | Mukherjee et al. |
| 2013/0296710 A1* | 11/2013 | Zuzak .................. A61B 5/0071 600/476 |
| 2014/0253714 A1 | 9/2014 | Weida |
| 2015/0051498 A1* | 2/2015 | Darty .................. G01N 21/255 600/477 |

OTHER PUBLICATIONS

K. Ruxton et al, "Mid-infrared hyperspectral imaging for the detection of explosive compounds", Proceedings of SPIE, vol. 8546, Oct. 30, 2012, p. 85460v, XP055216499, ISSN: 0277-786X, DOI: 10.1117/12.971185 abstract; section 2.1; figure 2.

The International Search Report and Written Opinion, PCT/US2015/040052, Daylight Solutions, Inc., Oct. 9, 2015. (Related application.).

* cited by examiner

SPECTRAL IMAGING OF A SAMPLE USING A PLURALITY OF DISCRETE MID-INFRARED WAVELENGTHS

RELATED APPLICATIONS

This application claims priority on U.S. Provisional Application Ser. No. 62/023,099, filed Jul. 10, 2014 and entitled "SPECTRAL IMAGING OF A SAMPLE USING A DISCRETE SET OF MID-INFRARED WAVELENGTHS". As far as permitted, the contents of U.S. Provisional Application Ser. No. 62/023,099 are incorporated herein by reference.

Additionally, this application is a continuation-in-part application of and claims priority on PCT Application Serial No. PCT/US15/11884, entitled "LOW-NOISE SPECTROSCOPIC IMAGING SYSTEM USING SUBSTANTIALLY COHERENT ILLUMINATION", filed on Jan. 18, 2015. PCT Application Serial No. PCT/US15/11884 claims priority on U.S. Provisional Application Ser. No. 61/929,050, filed Jan. 18, 2014 and entitled "LOW-NOISE SPECTROSCOPIC IMAGING SYSTEM USING SUBSTANTIALLY COHERENT ILLUMINATION". As far as permitted, the contents of PCT Application Serial No. PCT/US15/11884 and U.S. Provisional Application Ser. No. 61/929,050 are incorporated herein by reference.

BACKGROUND

Almost all materials have a unique mid-infrared spectrum, which describe absorption features that relate to the vibrational modes of chemical moieties within molecules.

SUMMARY

A method for spectrally analyzing an unknown sample includes (i) providing a spatially homogeneous region of the unknown sample; (ii) directing a plurality of interrogation beams at the spatially homogeneous region with a laser source, (iii) acquiring a separate output image of the unknown sample while the unknown sample is illuminated by each of the interrogation beams with an image sensor; and (iv) analyzing less than fifty output images to analyze whether a characteristic is present in the unknown sample with a control system that includes a processor. In this embodiment, each of the interrogation beams is nominally monochromatic and has a different interrogation wavelength that is in the mid-infrared spectral range. Further, the image sensor senses light in the mid-infrared spectral range.

As an overview, the number of different wavelengths in the mid-infrared spectral range required to accurately classify different sample classes and/or to distinguish different samples within a class can be significantly reduced to a very small number of interrogation wavelengths that provide the greatest variance between class types. With the present invention, the unknown sample is spectrally analyzed using the predetermined, relatively small number of specifically chosen interrogation wavelengths. As a result thereof, the unknown sample can be spectrally analyzed relatively quickly, the overall throughput can be increased, and the overall complexity is reduced because a much smaller number of spectral images are generated and analyzed.

As utilized herein, the term "mid-infrared spectral region" or "MIR spectral region" shall mean and include the spectral region or spectral band of between approximately two and twenty micrometers (2-20 μm) or wavelengths of between approximately five thousand and five hundred (5000-500 $cm^{-1}$). The MIR spectral range is particularly useful to spectroscopically interrogate the unknown sample since many samples are comprised of molecules or groups of molecules that have fundamental vibrational modes in the MIR range, and thus present strong, unique absorption signatures within the MIR range.

In one embodiment, the unknown sample can be accurately analyzed using less than thirty output images. In another embodiment, the unknown sample can be accurately analyzed using less than twenty output images.

Additionally, the method can include analyzing a known sample to identify a plurality of diagnostic spectral features, each diagnostic spectral feature being present at a different diagnostic wavelength in the mid-infrared spectral region. In this embodiment, each interrogation wavelength corresponds to a different one of the diagnostic wavelengths.

For example, the step of acquiring a separate output image can include capturing a plurality of separate preliminary images for each interrogation beam, and using the separate preliminary images to determine the separate output image for each interrogation beam. Alternatively, the step of acquiring a separate output image can include modulating the wavelength of the interrogation beam while capturing the corresponding output image.

In another embodiment, a first known sample and a second known sample that is different from the first known sample are analyzed to identify the plurality of diagnostic spectral features. In this embodiment, each diagnostic spectral feature is present at a different diagnostic wavelength in the mid-infrared spectral region.

In another embodiment, the present invention is directed to a method for spectrally analyzing an unknown sample, the method comprising the steps of: (i) identifying less than fifty diagnostic spectral features in a known sample, each diagnostic spectral feature being present at a different diagnostic wavelength in the mid-infrared spectral region; (ii) directing a plurality of interrogation beams at the unknown sample with a laser source, each interrogation wavelength corresponding to a different one of the diagnostic wavelengths; (iii) acquiring a separate output image of the unknown sample while the unknown sample is illuminated by each of the interrogation beams with an image sensor; and (iv) analyzing less than fifty output images to analyze whether a characteristic is present in the unknown sample with a control system that includes a processor.

In yet another embodiment, the present invention is directed toward an analysis assembly that includes a mid-infrared light source, an image sensor, and a control system. The image sensor senses light in the mid-infrared spectral region. The control system controls the mid-infrared light source to direct a plurality of interrogation beams toward the unknown sample, each of the plurality of interrogation beams having a different interrogation wavelength that corresponds to one of the diagnostic wavelengths. Additionally, the control system controls the image sensor to capture an output image of the unknown sample at the interrogation wavelength for each of the plurality of interrogation beams. Further, the control system evaluates less than fifty output images to analyze the unknown sample. In certain embodiments, the evaluation of the less than fifty output images is utilized to provide a characterization of the unknown sample.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION

Figure 1A:
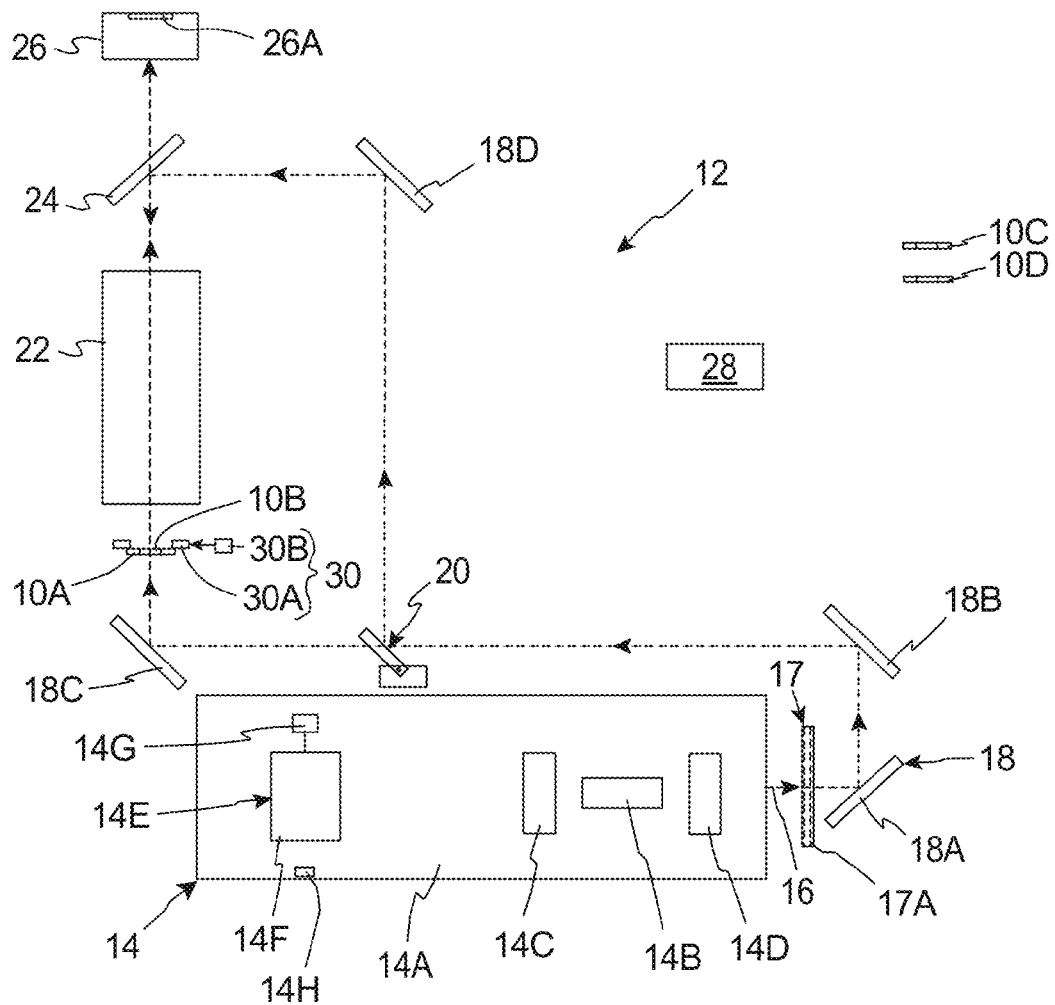
FIG. 1A is a simplified schematic illustration of a sample and an analysis assembly having features of the present invention.

FIG. 1A is simplified schematic illustration of an unknown sample 10A (e.g., a test sample), and an analysis assembly 12 having features of the present invention. In particular, the analysis assembly 12 can be used to rapidly and efficiently analyze and evaluate one or more characteristics of the unknown sample 10A. For example, in one non-exclusive embodiment, the analysis assembly 12 uses tunable laser radiation to rapidly spectrally interrogate and identify one or more characteristics of the unknown sample 10A. The present analysis assembly 12 and method provides increased sample throughput, while requiring minimal spectral expertise to operate. This will allow for the analysis assembly 12 to be used in both clinical and industrial applications.

The unknown sample 10A can be a variety of things, including mammalian blood, mammalian blood serum, mammalian cells, mammalian tissue, mammalian biofluids, microorganisms, mammalian blood plasma, and their animal counterparts; plant matter; explosive residues; powders; liquids; solids; inks; and other materials commonly analyzed using spectroscopy and microscopy. More particularly, in certain non-exclusive applications, the unknown sample 10A can be human blood serum and/or human connective tissue. In such applications, the analysis assembly 12 can be utilized for rapid screening of the unknown sample 10A for the presence of one or more characteristics. As non-exclusive examples, the characteristic can be a disease (e.g. the presence of cancer) and/or other health-related condition of the unknown sample 10A. Additionally and/or alternatively, the characteristic can include a property of the unknown sample 10A, the composition of the unknown sample 10A, and/or the identification of the unknown sample 10A. As other examples, the characteristic can be for the presence of explosive residues and/or other dangerous substances.

In certain embodiments, the unknown sample 10A is prepared to improve the accuracy of the spectral analysis of the unknown sample 10A. For example, the unknown sample 10A can be prepared to have a spatially homogeneous region 10B that is analyzed.

As used herein, the term "spatially homogeneous region" shall mean and include a region in the sample that is substantially structurally homogenous (or substantially structurally uniform). For example, a region of the sample can be considered substantially structurally homogeneous if the region has relatively little scattering at the discrete wavelengths in which the sample is analyzed. In one example, relatively little scattering shall mean when interrogation wavelengths have shifted less than 10 $cm^{-1}$ than expected. More specifically, in one example, for a serum sample, relatively little scattering shall mean when interrogation wavelengths have shifted less than 10 $cm^{-1}$ than expected. Depending on the sample, in alternative, non-exclusive embodiments, relatively little scattering shall mean when interrogation wavelengths have shifted less than 5, 6, 7, 8, 9, 11, 12, 13, or 15 $cm^{-1}$ than expected. In ideal situations, when the sample shows little scattering, the discrete wavelength paradigm works best and the smallest number of wavelengths can be used. It should be noted that the preferred maximum level of scattering will depend upon the material and composition of the sample. The distorting or scattering effects that alter spectral features are predominant when the interrogating light is of a wavelength that is on the same order of size as the sample material, or any of the sample's internal components, whether physical or chemical in nature. However, distortion can also be manifested when a change in refractive index occurs (i.e. going from the edge of a sample material to the outside environment, or from a particle composed within a sample material to adjacent area of material with no particles).

Conversely, the region of the sample is not substantially structurally uniform (e.g., the region is structurally heterogeneous), for example, when it includes particles, droplets, bubbles, density fluctuations, refractive index fluctuations, surface roughness, intra-cellular structures, tissue structures and so on.

In certain embodiments, it is desired that the samples are prepared to have a relatively large structurally homogeneous region.

It should be noted that in non-ideal situations, when scattering or diffraction is bad (e.g. interrogation wavelengths have shifted greater than 10 cm$^{-1}$ than expected), a smaller number of wavelengths than the full spectrum can still be used to segment classes of samples.

In certain applications, the unknown sample 10A can be thin enough to allow study through transmission of an illumination beam, e.g., an infrared illumination beam, through the unknown sample 10A (i.e. in transmission mode). Additionally, in other applications, the unknown sample 10A can be an optically opaque sample that is analyzed through reflection of an illumination beam, e.g., an infrared illumination beam, by the sample (i.e. in reflection mode). Further, in still other applications, the unknown sample 10A can be thin enough to allow study through transflection of an illumination beam, e.g., an infrared illumination beam can pass through the sample, reflect on the surface of a reflective substrate, and again pass through the sample, the illumination beam being double attenuated. For example, in the embodiment illustrated in FIG. 1A, the analysis assembly 12 can alternatively be utilized in transmission mode and/or reflection mode, and data can be acquired using a transmission, reflection, and/or transflection methodology.

As an overview, one or more training ("known") samples 10C, 10D (illustrated as boxes away from the analysis assembly 12) are first spectrally analyzed in the mid-infrared spectral region. These known samples 10C, 10D can in addition be prepared to each provide a spatially homogeneous region. The analysis of the one or more known samples 10C, 10D in the mid-infrared spectrum can include absorbance measurements from many thousands of alternative wavelengths dependent on the spectral resolution and spectral range probed. Spectral differences between classes of samples 10C, 10D and/or within a class of samples 10C, 10D having different biochemical characteristics can be apparent across the full range of wavelengths probed. The spectral analysis of the known samples 10C, 10D can be performed using the same analysis assembly 12 or on a different analysis assembly 12.

As provided herein, the number of wavelengths in the mid-infrared spectral range required to accurately classify different sample classes and/or to distinguish different samples within a class can be significantly reduced to a very small number of interrogation wavelengths that provide the greatest variance between class types. More specifically, as provided herein, the spectral results of the known samples 10C, 10D can be reviewed to identify a relatively small number of diagnostic spectral features of the characteristics in the known samples 10C, 10D. Each diagnostic spectral feature is present at a different diagnostic wavelength in the mid-infrared spectral region. Typically, as provided herein, depending on the sample and the characteristic to be identified, as alternative non-exclusive examples, less than approximately fifteen, twenty, twenty-five, thirty, thirty-five, forty, forty-five, fifty, sixty, seventy, eighty, or ninety different diagnostic spectral features are identified. Thus, in alternative non-exclusive examples, less than approximately fifteen, twenty, twenty-five, thirty, thirty-five, forty, forty-five, fifty, sixty, seventy, eighty, or ninety different diagnostic wavelengths are identified.

In certain embodiments, the analysis assembly 12 is controlled to spectrally analyze the unknown sample 10A using a predetermined, relatively small number of interrogation beams, with each interrogation beam having a different interrogation wavelength in the mid-infrared range. In this embodiment, each interrogation wavelength corresponds and/or is equal to one of the different diagnostic wavelengths. With this design, a spectral image can be acquired for each interrogation beam to analyze the unknown sample 10A and identify if the characteristic is present. As a result thereof, the user of the analysis assembly 12 is able to achieve significant gains in speed of the spectral analysis of the unknown sample 10A, and thus in overall throughput, as well as substantially reducing the overall complexity of the processing requirements with a much smaller number of spectral images to be captured within the analysis assembly 12.

As utilized herein, the term "diagnostic spectral feature" shall mean and include a distinctive spectral feature that is identified through a complete spectral analysis of the known samples 10C, 10D. The diagnostic spectral feature can be selected based on an absorbance value recorded at each of a plurality of test wavelengths during the spectral analysis of the known sample. Alternatively, the diagnostic spectral features can be selected based on a transmittance value or another appropriate value recorded at a plurality of wavelengths during the spectral analysis of the known sample. The diagnostic spectral features can be identified manually or by computer analysis (e.g. with the analysis assembly 12).

The term "diagnostic wavelength" shall mean the wavelength range in which the diagnostic spectral feature is centered or present. The width of the diagnostic spectral feature can vary. For example, if the diagnostic spectral feature has a width of ten wavenumbers, then there is very little variance in the diagnostic spectral feature over 1 cm$^{-1}$. In this example, the diagnostic wavelength can have a range of ten wavenumbers.

As provided herein, each interrogation beam is nominally monochromatic and has a different interrogation wavelength that is in the mid-infrared spectral range. Each interrogation beam can include one or more pulses of light or a continuous pulse of light. Further, the center wavelength of the interrogation beam can be modulated slightly over time. In one embodiment, multiple images are captured while the interrogation beam is modulated and these multiple images are averaged. For example, images can be captured at −0.5, 0, and +0.5 about a target wavelength and the three images can be averaged. Alternatively, a single image can be captured while the interrogation beam is modulated. For example, an image can be captured while the illumination beam is modulated plus or minus 0.5 wavelengths about a target wavelength. In these examples, the interrogation beam is nominally monochromatic and has an interrogation wavelength that is a range that is centered on the target wavelength.

Each interrogation wavelength can be a single wavelength generated by the analysis assembly 12, an average of several nearby wavelengths generated by the analysis assembly 12, and/or a range of several nearby wavelengths generated by the analysis assembly 12 near a target wavelength. Each interrogation wavelength corresponds to and is equal to a separate one of the diagnostic wavelengths. Further, the interrogation wavelengths are spaced apart. Typically, the interrogation wavelengths are unevenly spaced apart from one another. It should be noted that the range of the interrogation wavelength can be due to fundamental linewidths of the laser light source. Alternatively, the range of the interrogation wavelength can be defined in terms of the diagnostic spectral feature being analyzed. For example, in the diagnostic spectral feature has a width of ten wavenumbers, then the illumination beam can be controlled to have an interrogation wavelength that varies or that is within ten wavenumbers.

The design of the analysis assembly 12 can be varied. As a non-exclusive example, the analysis assembly 12 can be a mid-infrared imaging microscope. A detailed discussion of suitable imaging microscopes are described in PCT Application Serial Nos. PCT/US12/61987, PCT/US14/33878 and PCT/US15/11884. As far as permitted, the contents of PCT Application Serial Nos. PCT/US12/61987, PCT/US14/33878 and PCT/US15/11884 are incorporated herein by reference. In one embodiment, as noted above, the analysis assembly 12 uses tunable laser radiation to interrogate one or more samples 10 in order to reveal characteristics ("properties") of the unknown sample 10A.

For example, in the embodiment illustrated in FIG. 1A, the analysis assembly 12 can include (i) a light source 14, e.g., a laser source, that generates the plurality of interrogation beams 16, each at a different interrogation wavelength, (ii) an illumination lens assembly 17, (iii) a plurality of spaced apart beam steerers 18 that steer the interrogation beams 16, (iv) an illumination switch 20 that is controlled to either direct the interrogation beams 16 at the unknown sample 10A in transmission mode or reflection mode, (v) an objective lens assembly 22, (vi) a beamsplitter 24, (vii) a light sensing device 26 that includes an image sensor 26A that senses light in the infrared, e.g., mid-infrared, spectral region and captures an infrared image, e.g., a mid-infrared image, of the unknown sample 10A; and (v) a control system 28 that controls the light source 14 to direct the interrogation beams 16 toward the unknown sample 10A. It should be appreciated that the analysis assembly 12 can be designed with more or fewer components than those specifically illustrated in FIG. 1A, and/or the components can be organized in another fashion than as illustrated in FIG. 1A.

The design of the laser source 14 can be varied to suit the specific requirements of the analysis assembly 12 and/or the characteristics of the unknown sample 10A that is to be analyzed. In certain embodiments, the laser source 14 emits the plurality of interrogation beams 16 that is usable for illuminating and analyzing the unknown sample 10A in transmission mode and/or in reflection mode. For example, in some such embodiments, the laser source 14 is a mid-infrared beam source that generates and emits the interrogation beams 16 that are in the mid-infrared spectral region.

Additionally, in certain alternative embodiments, the laser source 14 can be a pulsed laser and/or a continuous wave (CW) laser. Moreover, in some embodiments, as provided herein, the laser source 14 can include one or more individual lasers, or laser modules, that target a single wavelength or span a portion or all of the desired mid-infrared spectral range.

Further, in one non-exclusive embodiment, the laser source 14 can be an external cavity laser that includes a laser frame 14A, a gain medium 14B, a cavity optical assembly 14C, an output optical assembly 14D, and a wavelength selective ("WS") feedback assembly 14E (e.g., a movable grating). The design of each of these components can be varied to achieve the requirements of the present invention.

The laser frame 14A provides a rigid support for the components of the laser source 14. In one embodiment, the laser frame 14A is a single mechanical ground plane that provides structural integrity for the laser source 14. In certain embodiments, the laser frame 14A is made of a rigid material that has a relatively high thermal conductivity.

In one, non-exclusive embodiment, the gain medium 14B directly emits the interrogation beams 16 without any frequency conversion. As non-exclusive examples, the gain medium 14B can be a Quantum Cascade (QC) gain medium, an Interband Cascade (IC) gain medium, or a mid-infrared diode. Alternatively, another type of gain medium 14B can be utilized.

In FIG. 1A, the gain medium 14B includes (i) a first facet that faces the cavity optical assembly 14C and the feedback assembly 14E, and (ii) a second facet that faces the output optical assembly 14D. In this embodiment, the gain medium 14B emits from both facets. In one embodiment, the first facet is coated with an anti-reflection ("AR") coating, and the second facet is coated with a reflective coating. The AR coating allows light directed from the gain medium 14B at the first facet to easily exit as a beam directed at the WS feedback assembly 14E; and allows the light beam reflected from the WS feedback assembly 14E to easily enter the gain medium 14B. The interrogation beams 16 exits from the second facet. The partly reflective coating on the second facet of the gain medium 14B reflects at least some of the light that is directed at the second facet of the gain medium 14B back into the gain medium 14B.

The cavity optical assembly 14C can be positioned between the gain medium 14B and the WS feedback assembly 14E along a lasing axis. The cavity optical assembly 14C collimates and focuses the beam that passes between these components. For example, the cavity optical assembly 14C can include a single lens or more than one lens.

The output optical assembly 14D is positioned between the gain medium 14B and one of the beam steerers 18 in line with the lasing axis to collimate and focus the interrogation beams 16 that exits the second facet of the gain medium 14B. For example, the output optical assembly 14D can include a single lens or more than one lens that are somewhat similar in design to the lens of the cavity optical assembly 14C.

The WS feedback assembly 14E reflects the beam back to the gain medium 14B, and is used to precisely select and adjust the lasing frequency of the external cavity and the wavelength of the pulses of light. In this design, the interrogation beams 16 may be tuned with the WS feedback assembly 14E without adjusting the gain medium 14B. Thus, with the external cavity arrangement disclosed herein, the WS feedback assembly 14E dictates what wavelength will experience the most gain and thus dominate the wavelength of the interrogation beams 16.

In some embodiments, the WS feedback assembly 14E includes a diffraction grating 14F and a grating mover 14G that selectively moves (e.g., rotates) the diffraction grating 14F to adjust the lasing frequency of the gain medium 14B and the interrogation wavelength of the interrogation beams 16. The diffraction grating 14F can be continuously monitored with an encoder 14H that provides for closed loop control of the grating mover 14G. With this design, the interrogation wavelength of the interrogation beams 16 can be selectively adjusted in a closed loop fashion so that the unknown sample 10A can be imaged at the many different, interrogation wavelengths.

It should be appreciated that laser-based analysis assemblies, such as described herein, can employ a variety of methods to rapidly switch between the plurality of interrogation wavelengths. These include techniques such as rapid tuning mechanisms, galvo-controlled mirrors to switch between different laser modules, or spectral beam combining techniques of multiple laser modules and subsequent time-division multiplexing of laser illumination.

Figure 1B:
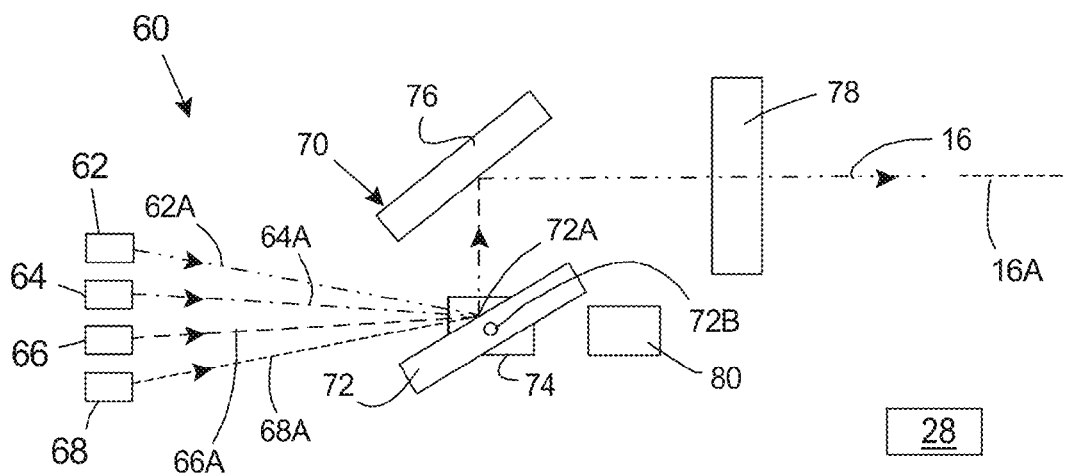
FIG. 1B is a simplified schematic top view illustration of a portion of a light source that can be used with the analysis assembly of FIG. 1A.

For example, FIG. 1B is a simplified schematic top view illustration of a portion of another embodiment of the light source 60 that can be used with the analysis assembly 12 of FIG. 1A. The design of the laser source 60 can be varied. In certain embodiments, the laser source 60 includes a laser frame (not shown in FIG. 1B), a plurality of laser modules 62, 64, 66, 68 (only four are illustrated), a beam selector assembly 70, and the control system 28 that cooperate to generate the interrogation beams 16. The design of each of these components can be varied pursuant to the teachings provided herein. Further, it should be noted that the laser source 60 can be designed with more or fewer components than described herein.

The laser frame supports at least some of the components of the laser source 60. In some embodiments, the laser modules 62, 64, 66, 68 and the beam selector assembly 70 can each be fixedly secured, in a rigid arrangement to the laser frame. Additionally, the control system 28 can be fixedly secured to the laser frame or the control system 28 can be separate from and external to the source frame.

The number and/or design of the laser modules 62, 64, 66, 68 can be varied to achieve a desired output wavelength range. In one embodiment, the laser source 60 includes four, spaced apart laser modules 62, 64, 66, 68. Alternatively, the laser source 60 can be designed to include more than four, or fewer than four laser modules 62, 64, 66, 68. In certain embodiments, each of the laser modules 62, 64, 66, 68 can be specifically designed to generate a different portion (or partly overlapping portion) of a predetermined wavelength range. Thus, as the desired predetermined wavelength range is increased, the number of laser modules 62, 64, 66, 68 can be increased, with each laser module 62, 64, 66, 68 generating a separate portion of the predetermined wavelength range.

As provided herein, in some embodiments, power is sequentially directed to (i) the first laser module 62 that can be adjusted to generate a first module beam 62A that spans a first range portion; (ii) the second laser module 64 that can be adjusted to generate a second module beam 64A that spans a second range portion; (iii) the third laser module 66 that can be adjusted to generate a third module beam 66A that spans a third range portion; and (iv) the fourth laser module 68 that can be adjusted to generate a fourth module beam 68A that spans a fourth range portion. With this design, the first beam 62A, the second beam 64A, the third beam 66A, and the fourth beam 68A can be sequentially used to provide the interrogation beams. It should be noted that the order of firing of the laser modules 62, 64, 66, 68 can be any arrangement.

Additionally, in certain embodiments, each laser module 62, 64, 66, 68 can have a corresponding director assembly (not shown) for precisely directing the module beams 62A, 64A, 66A, 68A at the beam selector assembly 70. The director assemblies can have any suitable design.

The beam selector assembly 70 selectively and alternatively directs one of the module beams 62A, 64A, 66A, 68A along an output beam axis 16A to provide the interrogation beams 16. In FIG. 1B, all of the module beams 62A, 64A, 66A, 68A are directed at the beam selector assembly 70 at once. This occurs when sufficient power is directed to all of the laser modules 62, 64, 66, 68 at the same time. Alternatively, sufficient power may be directed to only one laser module 62, 64, 66, 68 at any given time. In such example, only one of the beams 62A, 64A, 66A, 68A will be directed at the beam selector assembly 70 at any given time.

The design of the beam selector assembly 70 can be varied to suit the requirements of the light source 60 and/or the analysis assembly 12. In this embodiment, the beam selector assembly 70 includes a beam selector 72, a selector mover 74, a selector redirector 76 (e.g. a turn mirror), and a selector lens 78 positioned on the output beam axis 16A to collimate the interrogation beams 16. The design of each of these components can be varied to achieve the design requirements of the laser source 60.

In certain embodiments, the beam selector 72 is a flat mirror having a mirror center surface 72A, and the selector mover 74 is a motor that moves (e.g., rotates) the beam selector 72 about a selector axis 72B. In one embodiment, the beam selector 72 and the selector mover 74 are a galvo assembly that include a flat, galvo mirror and a galvo mover that selectively moves (e.g., rotates the galvo mirror) in a closed loop fashion. With this design, the movement of the beam selector 72 about a single axis is used to select the module beam 62A, 64A, 66A, 68A that is used for the interrogation beams 16. Further, with this design, the galvo can be controlled to make real time corrections in the position of the beam selector 72 to correct if one of the module beams 62A, 64A, 66A, 68A wanders. Alternatively, the beam selector 72 can be a multifaceted polygonal mirror (e.g., a Chinook polygonal mirror like that is sold by Lincoln Laser) that is rapidly rotated by the selector mover 74.

Additionally, the beam selector assembly 70 can include a selector feedback device 80 that additionally measures and monitors the position of the mirror 72 and provides a position signal to the control system 28 that can be used for closed loop control of the selector mover 74. As non-exclusive examples, the selector feedback device 80 can be an optical encoder, or a Hall type sensor.

In the embodiment shown in FIG. 1B, the module beams 62A, 64A, 66A, 68A are directed at the beam selector assembly 70 at different angles. With such design, the selector mover 74 can selectively position the beam selector 72 at alternative positions to redirect (select) one of the beams 62A, 64A, 66A, 68A at the selector redirector 76 which redirects that beam along the output beam axis 16A as the interrogation beams 16. The alternative positions can be indexed and saved in the control system 28. With this design, the beam selector 72 can be positioned and the laser modules 62, 64, 66, 68 can be controlled to generate the desired interrogation beams 16.

In certain embodiments, each of the director assemblies can direct the corresponding module beam 62A, 64A, 66A, 68A approximately at the mirror center surface 72A when the beam selector 72 is in the appropriate corresponding alternative position.

The control system 28 controls the operation of the laser modules 62, 64, 66, 68, and the beam selector assembly 70 to control the characteristics of the interrogation beams 16. For example, the control system 28 can control the current that is directed to each laser module 62, 64, 66, 68, and the beam selector assembly 70 to control the wavelength of the interrogation beams 16.

Returning now to FIG. 1A, in certain embodiments, the interrogation beams 16 exiting the beam source 14 can be transformed and/or directed toward and impinging on the unknown sample 10A, at least in part, with the illumination lens assembly 17. In one embodiment, the illumination lens assembly 17 can include one or more refractive lenses 17A (only one is illustrated in phantom) that transform the interrogation beams 16 and/or assist in directing the interrogation beams 16 at the unknown sample 10A. Moreover, the illumination lens assembly 17 can be refractive in the MIR range.

For example, the illumination lens assembly 17 can be utilized to focus and/or adjust the size of the interrogation beams 16, i.e. to increase (magnify) or decrease the size of the interrogation beams 16, so that the interrogation beams 16 has a desired size and beam profile on the unknown sample 10A. In certain embodiments, the size of an illuminated area (not shown) of the unknown sample 10A can be tailored to correspond to the design of the light sensing device 26 and the objective lens assembly 22.

As shown in FIG. 1A, the plurality of beam steerers 18 can be utilized to steer the interrogation beams 16 so that the interrogation beams 16 is directed toward the unknown sample 10A as desired. For example, in one application, the illumination switch 20 can be adjusted, e.g., moved out of the path of the interrogation beams 16, so as to enable the interrogation beams 16 to be directed at the unknown sample 10A with one or more of the beam steerers 18, with the unknown sample 10A then being spectroscopically analyzed in transmission mode. More particularly, in one non-exclusive embodiment, when in transmission mode based on the adjustment of the illumination switch 20, the interrogation beams 16 can be directed consecutively by a first beam steerer 18A, a second beam steerer 18B and a third beam steerer 18C so that the interrogation beams 16 are directed toward and through the unknown sample 10A. Alternatively, the plurality of beam steerers 18 can be positioned and/or utilized in a different manner to direct the interrogation beams 16 toward the unknown sample 10A so the unknown sample 10A can be spectroscopically analyzed in transmission mode.

In another application, the illumination switch 20 can be adjusted, e.g., moved into the path of the interrogation beams 16, so as to enable the interrogation beams 16 to be directed at the unknown sample 10A with one or more of the beam steerers 18, with the unknown sample 10A then being spectroscopically analyzed in reflection mode. As illustrated, in one embodiment, at least a portion of the interrogation beams 16 can be further directed through use of the beamsplitter 24 in order to be properly directed toward the unknown sample 10A for spectroscopic analysis of the unknown sample 10A in reflection mode. More particularly, in the embodiment illustrated in FIG. 1A, when in reflection mode based on the adjustment of the illumination switch 20, the interrogation beams 16 can be directed consecutively by the first beam steerer 18A, the second beam steerer 18B, the illumination switch 20, a fourth beam steerer 18D and the beamsplitter 24 so that the interrogation beams 16 is directed toward and reflected off of the unknown sample 10A. Alternatively, the plurality of beam steerers 18 and/or the beamsplitter 24 can be positioned and/or utilized in a different manner to direct the interrogation beams 16 toward the unknown sample 10A so the unknown sample 10A can be spectroscopically analyzed in reflection mode.

The design of the beam steerers 18 can be varied. In one embodiment, each of the beam steerers 18 can be a mirror (reflective in the desired wavelength spectrum) which is positioned so as to redirect the path of the interrogation beams 16 by approximately ninety degrees. Alternatively, one or more of the beam steerers 18 can have a different design and/or the beam steerers 18 can be positioned so as to redirect the path of the interrogation beams 16 by greater than or less than approximately ninety degrees. Still alternatively, one or more of the beam steerers 18 can include a curved mirror that conditions the interrogation beams 16 (i) to complement the illumination lens assembly 17, or (ii) to allow for the elimination of a portion or all of the illumination lens assembly 17. Further, the beam steerers 18 may also include one or more electrically controllable angular adjustments.

As noted, the illumination switch 20 can be selectively adjusted to enable the interrogation beams 16 to be alternatively utilized for spectroscopic analysis of the unknown sample 10A in transmission mode and/or reflection mode. For example, in the embodiment illustrated in FIG. 1A, when the illumination switch 20 is moved out of the path of the interrogation beams 16, the interrogation beams 16 can be utilized for spectroscopic analysis of the unknown sample 10A in transmission mode. Additionally, when the illumination switch 20 is moved into the path of the interrogation beams 16, and thus reflects the interrogation beams 16, e.g., by approximately ninety degrees, the interrogation beams 16 can be utilized for spectroscopic analysis of the unknown sample 10A in reflection mode. Alternatively, the design and function of the illumination switch 20 can be reversed such that when the illumination switch 20 is moved into the path of the interrogation beams 16, and thus reflects the interrogation beams 16, e.g., by approximately ninety degrees, the interrogation beams 16 can be utilized for spectroscopic analysis of the unknown sample 10A in transmission mode; and when the illumination switch 20 is moved out of the path of the interrogation beams 16, the interrogation beams 16 can be utilized for spectroscopic analysis of the unknown sample 10A in reflection mode.

In some embodiments, as shown, the analysis assembly 12 can further include a stage assembly 30. In such embodiments, the stage assembly 30 retains the unknown sample 10A, and can be used to properly position the unknown sample 10A or alternatively the known samples 10C, 10D. For example, the stage assembly 30 can include a stage 30A that retains unknown sample 10A, and a stage mover 30B that selectively moves the stage 30A and the unknown sample 10A. For example, the stage mover 30B can include one or more actuators. Additionally and/or alternatively, the stage 30A can be manually positioned as desired.

In certain embodiments, the objective lens assembly 22 can include one or more refractive lenses such that the objective lens assembly 22 is optimized for coherent light, in the MIR spectral range. More specifically, the objective lens assembly 22 can be used in conjunction with the MIR laser source 14 that generates the coherent laser beam 16 that is in the MIR spectral range and that is directed at the unknown sample 10A. The laser beam 16 may traverse the objective lens assembly 22 prior to impinging on the unknown sample 10A, as in the case where the analysis assembly 12 is being utilized in reflection mode; or the laser beam 16 may impinge on the unknown sample 10A prior to traversing the objective lens assembly 22, as in the case where the analysis assembly 12 is being utilized in transmission mode. Depending upon the design, the objective lens assembly 22 can collect the light from the laser beam 16 that is either reflected off of or transmitted through the unknown sample 10A, and can image that light onto the light sensing device 26.

Additionally, in some embodiments, the objective lens assembly 22 can be optimized for the entire MIR spectral range, or only a portion of the MIR spectral range.

As noted above, in some embodiments, the beamsplitter 24 can be utilized to redirect at least a portion of the interrogation beams 16 toward the unknown sample 10A so that the unknown sample 10A can be spectroscopically analyzed in reflection mode. Additionally, as illustrated in FIG. 1A, at least a portion of the light from the interrogation beams 16 that is either reflected off of or transmitted through the unknown sample 10A, and that then traverses the objective lens assembly 22, can then be transmitted through the beamsplitter 24 before being imaged onto the light sensing device 26.

The light sensing device 26 receives and/or senses light from the interrogation beams 16 that is directed toward the light sensing device 26 after being transmitted through or reflected off of the unknown sample 10A. More particularly, in certain embodiments, the light sensing device 26 can be an infrared camera that includes an image sensor 26A that senses infrared light and converts the infrared light into an array of electronic signals that represents an image of the unknown sample 10A. In certain embodiments, the image sensor 26A includes a two-dimensional array of photosensitive elements (pixels) (e.g., a focal plane array (FPA)) that are sensitive to the wavelength of the interrogation beams 16, i.e. that are sensitive to the infrared region of the electromagnetic spectrum. Additionally, the two-dimensional array of pixels can be used to construct a two-dimensional image including the two-dimensional array of data (data at each pixel). The spacing between the pixel elements is referred to as the pitch of the array. As non-exclusive examples, the two-dimensional array can include approximately 640×480; 320×240; 480×480; 80×60; 1080×720; 120×120; 240×240; or 480×640 pixels, with pixel sizes ranging from one µm up to two hundred µm.

For example, if the interrogation beams 16 are in the MIR range, the image sensor 26A is a MIR imager. More specifically, if the interrogation beams 16 is in the infrared spectral region from two to twenty µm, the image sensor 26A is sensitive to the infrared spectral region from two to twenty µm. In certain alternative embodiments, the light sensing device 26 and/or the image sensor 26A can have a measurement band that is approximately equal to the entire MIR spectral range; or the light sensing device 26 and/or the image sensor 26A can have a measurement band is approximately equal to a predetermined desired range within the MIR spectral range. Further, in certain embodiments, the light sensing device 26 can block and not sense light outside the desired measurement band. Thus, it should be appreciated that the design of the light sensing device 26 can adjusted to match the desired requirements of the system.

Non-exclusive examples of suitable infrared image sensors 26A include (i) vanadium oxide (VOx) microbolometer arrays such as the FPA in the FLIR Tau 640 infrared camera that are typically responsive in the seven to fourteen µm spectral range; (ii) mercury cadmium telluride (HgCdTe or MCT) arrays such as those in the FLIR Orion SC7000 Series cameras that are responsive in the 7.7 to 11.5 µm spectral range; (iii) indium antimonide (InSb) arrays such as those in the FLIR Orion SC7000 Series cameras that are responsive in the 1.5 to 5.5 µm spectral range; (iv) indium gallium arsenide (InGaAs); (v) uncooled hybrid arrays involving VOx and other materials from DRS that are responsive in the two to twenty µm spectral range; or (vi) any other type of image sensor that is designed to be sensitive to infrared light in the two to twenty µm range and has electronics allowing reading out of each element's signal level to generate a two-dimensional array of image information.

The control system 28 controls the various components of the analysis assembly 12 and includes one or more processors and/or electronic data storage devices. For example, the control system 28 can control one or more components of the analysis assembly 12 and/or receive information from the pixels of the IR camera, i.e. the light sensing device 26, and generate the images of the unknown sample 10A. Additionally, the control system 28 can further be utilized to evaluate spectral images of the unknown sample 10A that have been captured by the image sensor 26A, i.e. at the various interrogation wavelengths to determine if the characteristic is present in the unknown sample 10A.

During use of the analysis assembly 12, it is generally desired to improve the spectral resolution and quality of the two-dimensional data of images of the unknown sample 10A. More specifically, in various applications, it is desired to inhibit various noise sources from adversely impacting the quality of the two-dimensional data of images of the unknown sample 10A.

For example, in certain applications, it can be desired to increase the apparent linewidth of the excitation source, so as to reduce coherence and, thus, inhibit adverse effects from multiple beam interference, e.g., etalons. More particularly, in some such applications, the control system 28 can control the MIR laser source 14 so as to generate an interrogation beam 16 that modulates the wavelength about the respective interrogation wavelength. Stated in another fashion, the control system 28 can control the tunable light source 14 to modulate the wavelength of the interrogation beam about and through each respective interrogation wavelength.

A separate image can be generated at individual steps or points during such wavelength modulation to provide a plurality of preliminary images. Subsequently, an output image is determined based on the plurality of preliminary images that have been generated.

Figure 2A:
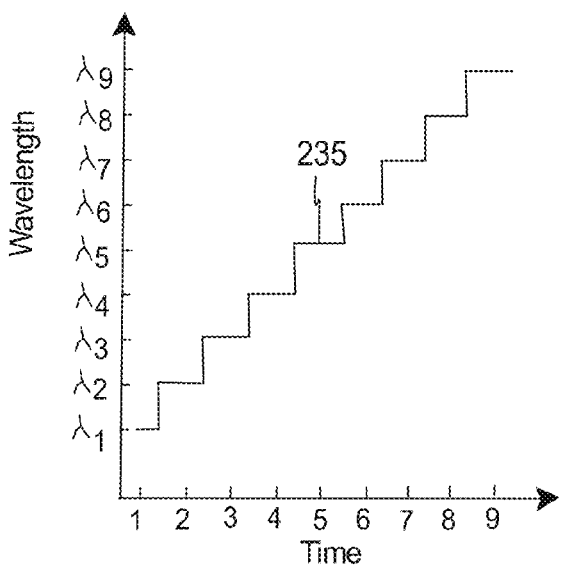
FIG. 2A is a graphical illustration of wavelength versus time during the generation of a set of preliminary images.
Figure 2B:
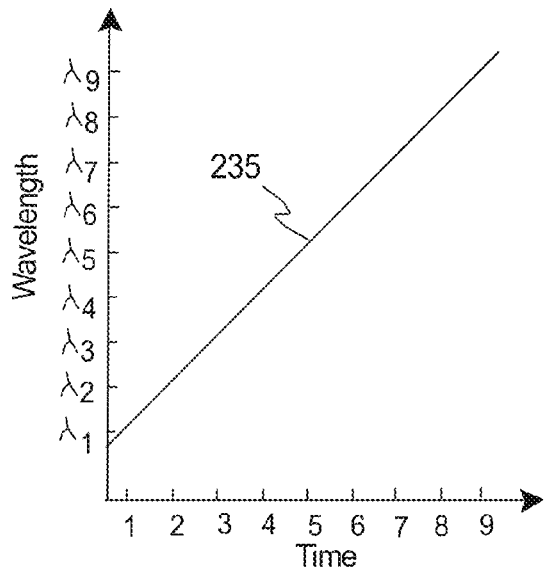
FIG. 2B is another graphical illustration of wavelength versus time during the generation of a set of preliminary images.

For example, FIG. 2A is a graphical illustration of wavelength versus time during the generation of such a plurality of preliminary images. As provided herein, the control system 28 (illustrated in FIG. 1A) can control the MIR laser source 14 (illustrated in FIG. 1A) to generate an interrogation beam 16 (illustrated in FIG. 1A) having a center wavelength that changes in a stepped pattern from a first wavelength to a ninth wavelength over time. Somewhat similarly, FIG. 2B is another graphical illustration of wavelength versus time during the generation of such a plurality of preliminary images. In this example, the control system 28 (illustrated in FIG. 1A) controls the MIR laser source 14 (illustrated in FIG. 1A) to generate an interrogation beam 16 (illustrated in FIG. 1A) having a center wavelength that changes in a linear fashion from a first wavelength to a ninth wavelength over time. It should be noted that the wavelength can be adjusted in another fashion than illustrated in FIGS. 2A and 2B.

Additionally, it should be appreciated that the number of individual wavelengths and the spacing between the individual wavelengths utilized in generating the preliminary images can be varied. For example, in certain non-exclusive alternative embodiments, the number of individual wavelengths of the interrogation beam 16 can vary over time one, two, three, four, five, six, or more individual wavelengths both above and below the interrogation wavelength. Additionally, in certain non-exclusive alternative embodiments, the spacing between the individual wavelengths within the interrogation beam 16 can be approximately 0.1, 0.2, 0.25, 0.33, 0.5, 0.67, 0.7, 1.0, 2.0 or 4.0 wavenumbers. It should be appreciated that the number of individual wavelengths and the spacing between the wavelengths within each interrogation beam 16 can be different than the specific examples listed above.

In the examples shown in FIGS. 2A and 2B, the first through ninth wavelengths make up the interrogation wavelength for this interrogation beam 16. In this simplified example, (i) at time one, the interrogation beam 16 has a first center wavelength; (ii) at time two, the interrogation beam 16 has a second center wavelength; (iii) at time three, the interrogation beam 16 has a third center wavelength; (iv) at time four, the interrogation beam 16 has a fourth center wavelength; (v) at time five, the interrogation beam 16 has a fifth center wavelength; (vi) at time six, the interrogation beam 16 has a sixth center wavelength; (vii) at time seven, the interrogation beam 16 has a seventh center wavelength; (viii) at time eight, the interrogation beam 16 has an eighth center wavelength; and (ix) at time nine, the interrogation beam 16 has a ninth center wavelength.

Additionally, in the examples illustrated in FIGS. 2A and 2B, the center-most, i.e. fifth, wavelength represents a target wavelength 235 that is at the approximate center of the interrogation wavelength. In this example, the interrogation wavelength is a distribution of wavelengths centered around the target wavelength 235.

Figure 2C:
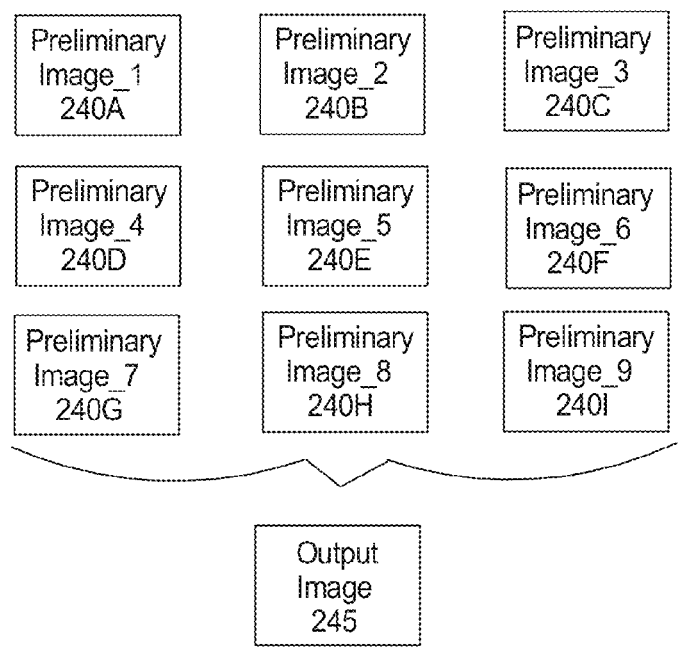
FIG. 2C illustrates a plurality of preliminary images used to generate an output image at an interrogation wavelength.

FIG. 2C illustrates a plurality of preliminary images 240A, 240B, 240C, 240D, 240E, 240F, 240G, 240H, 240I that can be used to generate an output image 245 for this interrogation beam.

In this simplified example, with reference to FIGS. 2A-2C, the analysis assembly 12 (illustrated in FIG. 1A) is controlled to (i) capture a first preliminary ("sampling") image 240A while illuminating the unknown sample 10A (illustrated in FIG. 1A) with light at the first center wavelength (at time=1); (ii) capture a second preliminary image 240B while illuminating the unknown sample 10A with light at the second center wavelength (at time=2); (iii) capture a third preliminary image 240C while illuminating the unknown sample 10A with light at the third center wavelength (at time=3); (iv) capture a fourth preliminary image 240D while illuminating the unknown sample 10A with light at the fourth center wavelength (at time=4); (v) capture a fifth preliminary image 240E while illuminating the unknown sample 10A with light at the fifth center wavelength (at time=5); (vi) capture a sixth preliminary image 240F while illuminating the unknown sample 10A with light at the sixth center wavelength (at time=6); (vii) capture a seventh preliminary image 240G while illuminating the unknown sample 10A with light at the seventh center wavelength (at time=7); (viii) capture an eighth preliminary image 240H while illuminating the unknown sample 10A with light at the eighth center wavelength (at time=8); and (ix) capture a ninth preliminary image 240I while illuminating the unknown sample 10A with light at the ninth center wavelength (at time=9).

Subsequently, the control system 28 uses one or more of the preliminary ("sampling") images 240A-240I to generate the output image 245 for this interrogation wavelength. The number of preliminary images 240A-240I used to generate the output image 245 can vary. More particularly, the number of preliminary images 240A-240I is based on the number of individual wavelengths within the interrogation beam 16 selected both above and below the interrogation wavelength.

Various alternative suitable methods can be utilized to combine the plurality of images, i.e. the preliminary images, generated at each of the individual wavelengths within the interrogation beam 16 to ultimately capture the desired output image 245 for the interrogation wavelength. For example, certain suitable methods are as illustrated and described in PCT Application Serial No. PCT/US15/11884, which, as noted above, is incorporated herein by reference.

In one non-exclusive embodiment, the preliminary images 240A-240I can be passed through a low-pass filter to generate the desired output image 245 for the specific interrogation wavelength. Stated in another manner, a low-pass filter is subsequently applied to the spectral response of each pixel in the respective preliminary images to create an output spectral image at a lower spectral resolution with less noise. As non-exclusive examples, the low-pass filter can utilize either a running average or Gaussian filter, which can be optionally followed by sub-sampling through decimation. One such method is to perform a simple average of the collected data points. Another method is to perform a simple average of the data points after extreme values are removed from the data set. Extreme values may be defined, for example, as those falling outside of a predefined multiple of the root-mean-square of the collection. Another method is to apply a low-pass filter over the data set, such as a Chebyshev filter. Yet another filtering method includes Fast Fourier Transform.

In this example, the influence of parasitic etalon components can be reduced and managed by discrete sampling, filtering, and decimation. First, a plurality of preliminary images 240A-240I are captured. Subsequently, the preliminary images 240A-240I are filtered to create a lower spectral resolution image that can optionally be sub-sampled (e.g., via decimation) to remove the redundant information from now being oversampled. Thus, a collection of spectral images is captured at multiple wavelengths in the neighborhood of the target wavelength. The collection of data points is then mathematically filtered so as to produce a single higher-fidelity data point for this interrogation wavelength.

In another embodiment, a reduction in spurious spectral artifacts in the output image can be achieved through fast source wavelength modulation and real-time detector averaging. Stated in another fashion, a reduction in noise can be achieved by rapidly tuning the light source 14 to generate an interrogation beam 16 having a rapidly varying center wavelength, and slowly capturing the output image with the image sensor 26A during the wavelength variation. With this design, for each interrogation wavelength, the analysis assembly 12, i.e. the control system 28 (illustrated in FIG. 1A) can dither the wavelength of the interrogation beam 16 during the capture of the respective output image.

Figure 3A:
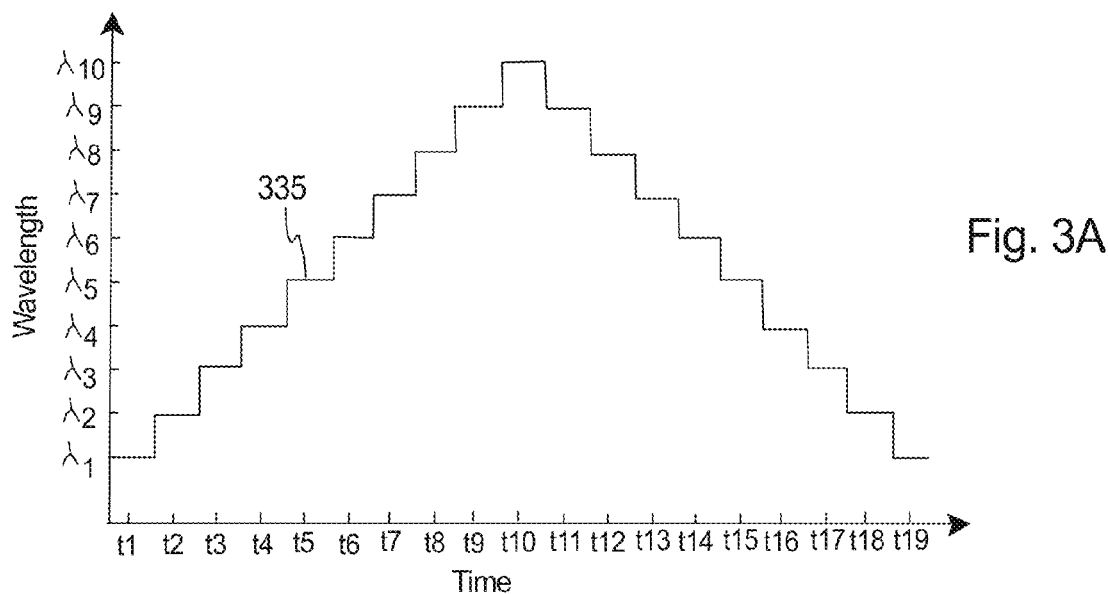
FIG. 3A is a graphical illustration of wavelength versus time during the generation of an output image.
Figure 3B:
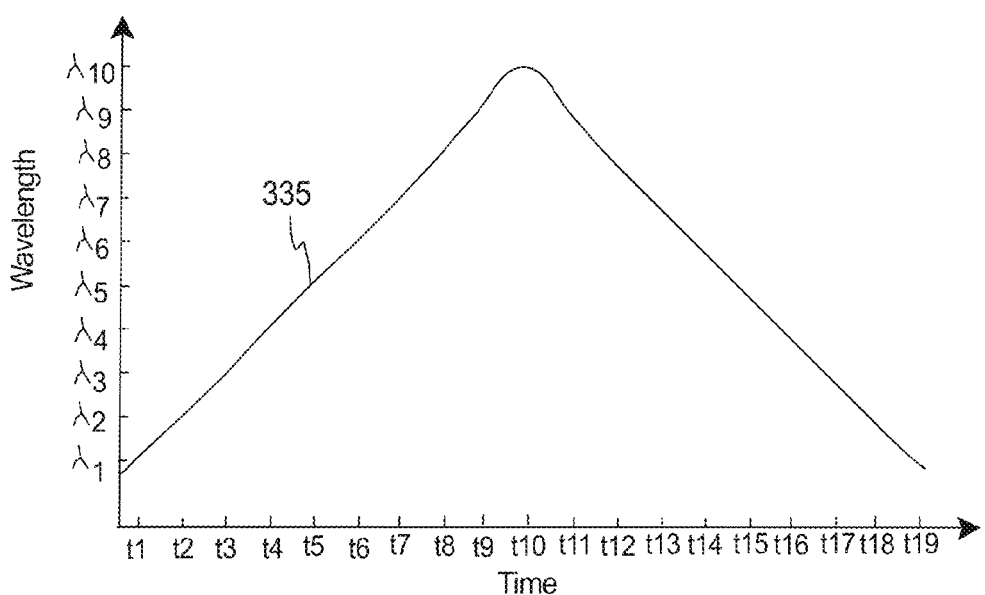
FIG. 3B is another graphical illustration of wavelength versus time during the generation of an output image.
Figure 3C:
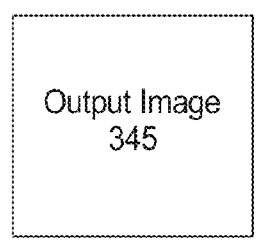
FIG. 3C illustrates an output image at an interrogation wavelength.

For example, FIG. 3A is a graphical illustration of wavelength versus time during the generation and/or capture of an output image 345 (illustrated in FIG. 3C). As provided herein, the control system 28 (illustrated in FIG. 1A) can control the MIR laser source 14 (illustrated in FIG. 1A) to generate an interrogation beam 16 (illustrated in FIG. 1A) having a center wavelength that changes in a stepped pattern from a first wavelength to a tenth wavelength and back to the first wavelength over time. Somewhat similarly, FIG. 3B is another graphical illustration of wavelength versus time during the generation and/or capture of an output image 345 (illustrated in FIG. 3C). In this example, the control system 28 (illustrated in FIG. 1A) controls the MIR laser source 14 (illustrated in FIG. 1A) to generate an interrogation beam 16 (illustrated in FIG. 1A) having a center wavelength that changes in a linear fashion from the first wavelength to the tenth wavelength and back to the first wavelength over time. It should be noted that the wavelength can be adjusted in another fashion than illustrated in FIGS. 3A and 3B.

In the examples illustrated in FIGS. 3A and 3B, the center-most, i.e. the fifth wavelength represents a target wavelength 335 that is at the approximate center of the interrogation wavelength. In this example, the interrogation wavelength is a distribution of wavelengths centered around the target wavelength 335.

FIG. 3C illustrates an output image 345 that is captured while the interrogation beam 16 (illustrated in FIG. 1A) is cycled from the first through tenth wavelength (first cycle) and back from the tenth wavelength to the first wavelength (second cycle). In this simplified example, with reference to FIGS. 3A-3C, the analysis assembly 12 (illustrated in FIG. 1A) is controlled to capture the output image 345 for the interrogation wavelength 335 (illustrated, for example, in FIGS. 3A and 3B) while the center wavelength of the interrogation beam 16 is varied (dithered) cycled twice between one and ten wavelengths.

Additionally, it should be appreciated that the range and amount (number of cycles) of dithering about the target wavelength 335 can be varied as desired. For example, in certain non-exclusive alternative embodiments, the dithering of the wavelengths about the target wavelength during the capture time can be approximately plus or minus 0.1, 0.25, 0.33, 0.5, 1.0, 2.0, 3.0, 4.0, 5.0, 6.0, 7.0 or 10.0 wavenumbers. Additionally, in some non-exclusive alternative embodiments, the wavelengths about the wavelength can be dithered through approximately one, two, three, four, five, ten, twenty, forty, fifty or one hundred cycles during the capture time of the output image 345 by the image sensor 26A (illustrated in FIG. 1A). It should be appreciated that the range of dithering and the number of cycles of dithering utilized can be different than the specific examples listed above.

As provided herein, the present invention provides a way to identify a few important, discrete wavelengths, i.e. diagnostic wavelengths, in the mid-infrared range that can be sequentially used to quickly collect data and screen the unknown sample 10A. This will improve the speed in which the unknown sample 10A is analyzed, because less data is acquired and less data has to be analyzed. Stated in another fashion, once a plurality of discriminatory, diagnostic wavelengths has been identified, the acquisition times can be markedly reduced because the analysis assembly 12 can be tuned to only acquire data from identified wavelengths of interest. Stated in still another fashion, a discrete wavelength system, such as with the laser-based analysis assembly 12 described herein, can probe just the plurality of specifically identified diagnostic wavelengths, thus greatly speeding the data acquisition time. Thus, such laser-based microscopy can realize high-throughput screening of samples, especially those composed of structurally homogenous materials.

It should be noted that the specific interrogation wavelengths utilized by the analysis assembly 12 will vary according to the unknown sample 10A that is being analyzed. For example, the plurality of interrogation wavelengths that are used to identify whether an unknown sample 10A is cancerous will differ from the plurality of interrogation wavelengths that are used to identify whether an unknown sample 10A includes explosives.

Additionally, the number of interrogation wavelengths, required to effectively analyze an unknown sample 10A can also vary according to the unknown sample 10A. As provided herein, the number of interrogation wavelengths utilized can be reduced from several thousands to less than one hundred discrete wavelengths. In alternative, non-exclusive embodiments, the number of diagnostic wavelengths in the mid-infrared range can be less than approximately ten, twenty, thirty, forty, fifty, sixty, seventy, eighty, or ninety. Moreover, in such embodiments, the control system 28 (illustrated in FIG. 1A) can be utilized to evaluate only the output images captured at each of the interrogation wavelengths. Stated in another manner, in such embodiments, in order to effectively analyze and characterize a given unknown sample 10A, the control system 28 can be utilized to evaluate less than ten, less than twenty, less than thirty, less than forty, less than fifty, less than sixty, less than seventy, less than eighty or less than ninety output images of the unknown sample 10A.

It should be appreciated that although in the process of limiting the number of output images that are evaluated, only the output images captured at the interrogation wavelengths need be evaluated in order to effectively characterize the unknown sample 10A. However, the control system 28 can also evaluate output images that have been captured at other wavelengths as well.

In one, non-exclusive, specific example, a human blood serum sample can be diagnosed as having a normal or brain cancer diagnosis using nine different interrogation wavelengths (nine different wavenumbers from approximately 900 wavenumbers in the mid-infrared range 900-1800 cm$^{-1}$ with a spectral resolution of 8 cm$^{-1}$). In this non-exclusive example, the interrogation wavelengths of (i) 6747.64 nanometers (wavenumber 1482 cm$^{-1}$), (ii) 6578.95 nanometers (wavenumber 1520 cm$^{-1}$), (iii) 6468.31 nanometers (wavenumber 1546 cm$^{-1}$), (iv) 6369.43 nanometers (wavenumber 1570 cm$^{-1}$), (v) 6250 nanometers (wavenumber 1600 cm$^{-1}$), (vi) 6134.97 nanometers (wavenumber 1630 cm$^{-1}$), (vii) 6045.95 nanometers (wavenumber 1654 cm$^{-1}$), (viii) 5931.20 nanometers (wavenumber 1686 cm$^{-1}$), and (ix) 5793.74 nanometers (wavenumber 1726 cm$^{-1}$) can be utilized. These interrogation wavelengths were identified using the procedures provided herein. It should be noted that other interrogation wavelengths can also be identified and utilized for this particular diagnosis.

Alternatively, in another non-exclusive, specific example, a human blood serum sample can be diagnosed as having a normal or brain cancer diagnosis using fourteen different interrogation wavelengths (fourteen different wavenumbers from approximately 900 wavenumbers in the mid-infrared range 900-1800 cm$^{-1}$ with a spectral resolution of 8 cm$^{-1}$). In this non-exclusive example, the interrogation wavelengths of (i) 10000 nanometers (wavenumber 1000 cm$^{-1}$); (ii) 9708.74 nanometers (wavenumber 1030 cm$^{-1}$); (iii) 9259.26 nanometers (wavenumber 1080 cm$^{-1}$); (iv) 6747.64 nanometers (wavenumber 1482 cm$^{-1}$), (v) 6578.95 nanometers (wavenumber 1520 cm$^{-1}$), (vi) 6468.31 nanometers (wavenumber 1546 cm$^{-1}$), (vii) 6369.43 nanometers (wavenumber 1570 cm$^{-1}$), (viii) 6250 nanometers (wavenumber 1600 cm$^{-1}$), (ix) 6134.97 nanometers (wavenumber 1630 cm$^{-1}$), (x) 6045.95 nanometers (wavenumber 1654 cm$^{-1}$), (xi) 5931.20 nanometers (wavenumber 1686 cm$^{-1}$), (xii) 5793.74 nanometers (wavenumber 1726 cm$^{-1}$); (xiii) 5767.01 nanometers (wavenumber 1734 cm$^{-1}$), and (xiv) 5649.72 nanometers (wavenumber 1770 cm$^{-1}$) can be utilized.

Expanding on this specific example, the potential improvements in speed of spectral analysis of the unknown sample 10A can be demonstrated. More specifically, a sample spectrally analyzed utilizing one hundred and ninety-nine discrete wavelengths that composed a mosaic of image frames had a data acquisition time of approximately forty-five minutes. When the number of discrete wavelengths was reduced to fourteen, the data acquisition time was reduced to approximately six-and-a-half minutes. Moreover, when the number of interrogation wavelengths was reduced to nine, the data acquisition time was reduced to approximately four minutes. As evidenced by such comparative analysis, the potential speed gains for the desired spectral analysis of an unknown sample can be fairly dramatic, with a corresponding decrease in processing complexity.

As provided herein, spectral features used for classification of different sample classes and/or for sample characterization within a given class can be, but are not limited to: (i) a measured absorbance value at a discrete wavelength; (ii) the integrated absorbance or area under the curve of a spectral region; (iii) the ratio of values reported in (i) and (ii) above; and/or (iv) any values in (i)-(iii) after the data has been transformed from absorbance to another format, for example a derivative.

Figure 4:
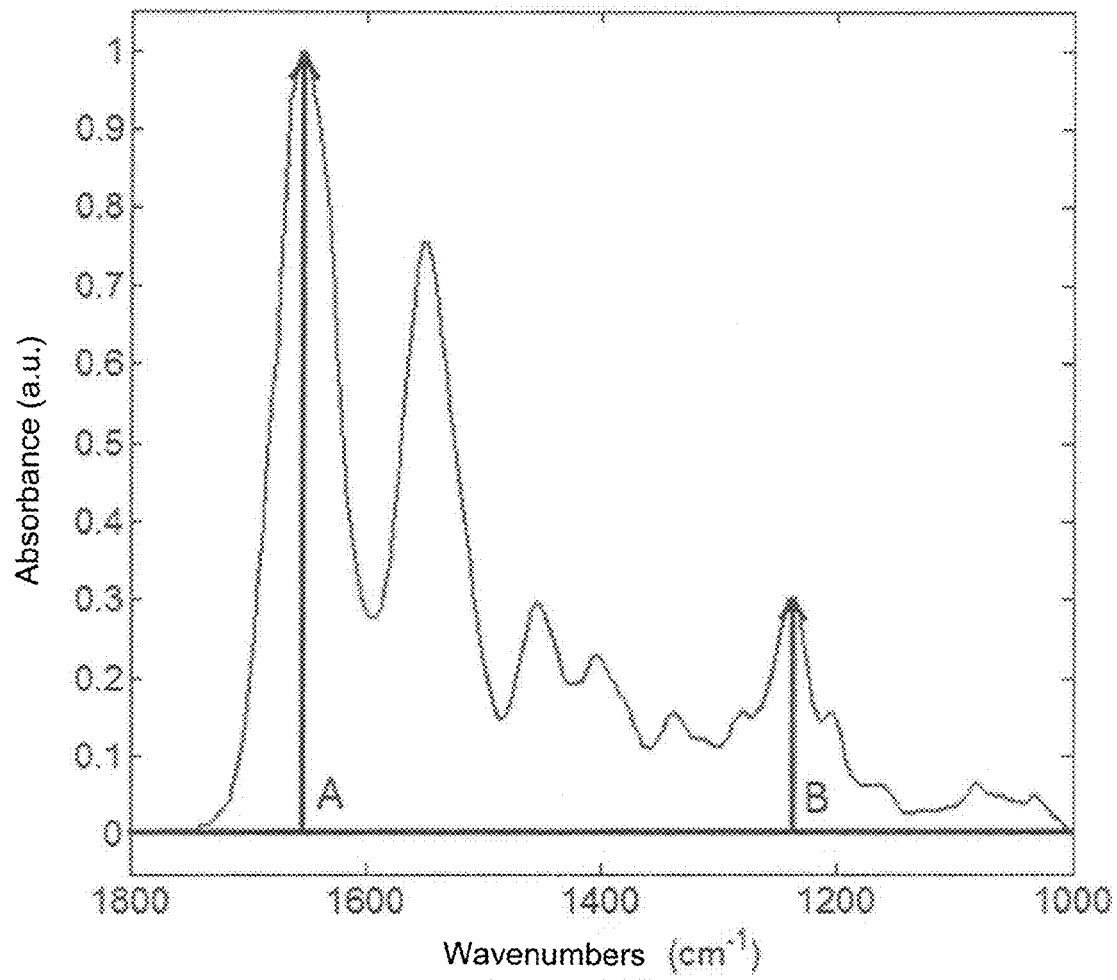
FIG. 4 is a graphical illustration of a normalized absorbance of a human connective tissue sample in a mid-infrared spectral region of 1000-1800 $cm^{-1}$.

FIG. 4 is a graphical illustration of a normalized absorbance of a sample in a mid-infrared spectral region of 10000 nanometers to 5555.56 nanometers (1000-1800 cm$^{-1}$). More particularly, FIG. 4 is a graph that illustrates the mid-infrared spectrum of a human connective tissue sample in the spectral region for the wavenumbers 1000-1800 cm$^{-1}$.

As provided herein, the full spectral range of a known sample can be acquired and used to identify a plurality of diagnostic wavelengths that provide the most diagnostic spectral features for that sample. For example, FIG. 4 illustrates the most diagnostic spectral features (large peaks) of the human connective tissue sample and the corresponding wavenumber. It should be noted that the diagnostic wavelength for each of the diagnostic spectral features can be determined with simple calculations from the wavenumber. Once these diagnostic spectral features are learned, only the plurality of diagnostic wavelengths that correspond to these diagnostic spectral features are needed to quickly identify subsequent possible samples of this type.

In one non-exclusive embodiment, as shown in FIG. 4, the absorbance values recorded at wavenumbers A and B could be used, at least in part, as features to provide characterization or classification of the sample. More specifically, in such embodiment, diagnostic spectral features can be found at approximately 6060.61 nanometers (1650 cm$^{-1}$) (wavelength A) and approximately 8064.52 nanometers (1240 cm$^{-1}$) (wavelength B). The calculated absorbance ratio for diagnostic wavelengths A and B (feature A/feature B) may also be used as a feature to provide characterization or classification of a sample.

It should be appreciated that additional appropriate diagnostic wavelengths, i.e. demonstrating strong diagnostic spectral features, can also be determined from one or more of the additional large peaks illustrated in FIG. 4. For example, as illustrated, certain additional large peaks are clearly shown in FIG. 4 between the wavelengths identified at diagnostic wavelength A and diagnostic wavelength B.

Figure 5:
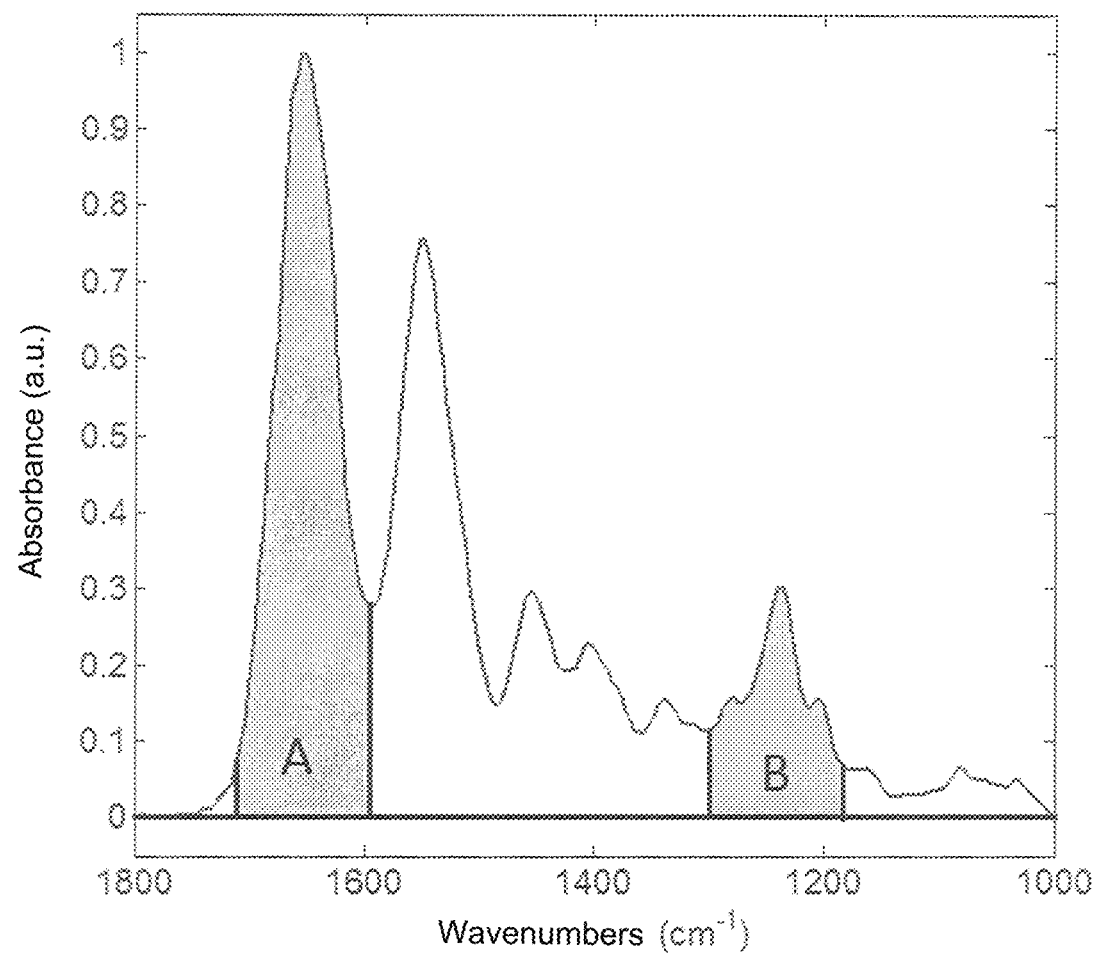
FIG. 5 is another graphical illustration of the normalized absorbance of the human connective tissue sample of FIG. 4 in the mid-infrared spectral region of 1000-1800 $cm^{-1}$.

FIG. 5 is another graphical illustration of the normalized absorbance of the human connective tissue sample of FIG. 4 in the mid-infrared spectral region of 1000-1800 cm$^{-1}$. In particular, FIG. 5 illustrates integrated absorbance values or areas under the curve for certain identified wavelengths. As non-exclusive examples, the integrated absorbance values or area under the curve recorded in spectral regions A and B could, for example, be used as features to provide characterization or classification of a sample. Alternatively, the ratio of calculated integrated absorbance values or area under the curves calculated for spectral regions A and B (feature A/feature B) may also be used as a feature to provide characterization or classification of a sample.

Additionally, as with the previous Figure, it should be appreciated that other integrated absorbance values can also be calculated related to other wavelengths that also represent large peaks in the overall absorbance curve for the full spectral range of the known human connective tissue sample.

Figure 6:
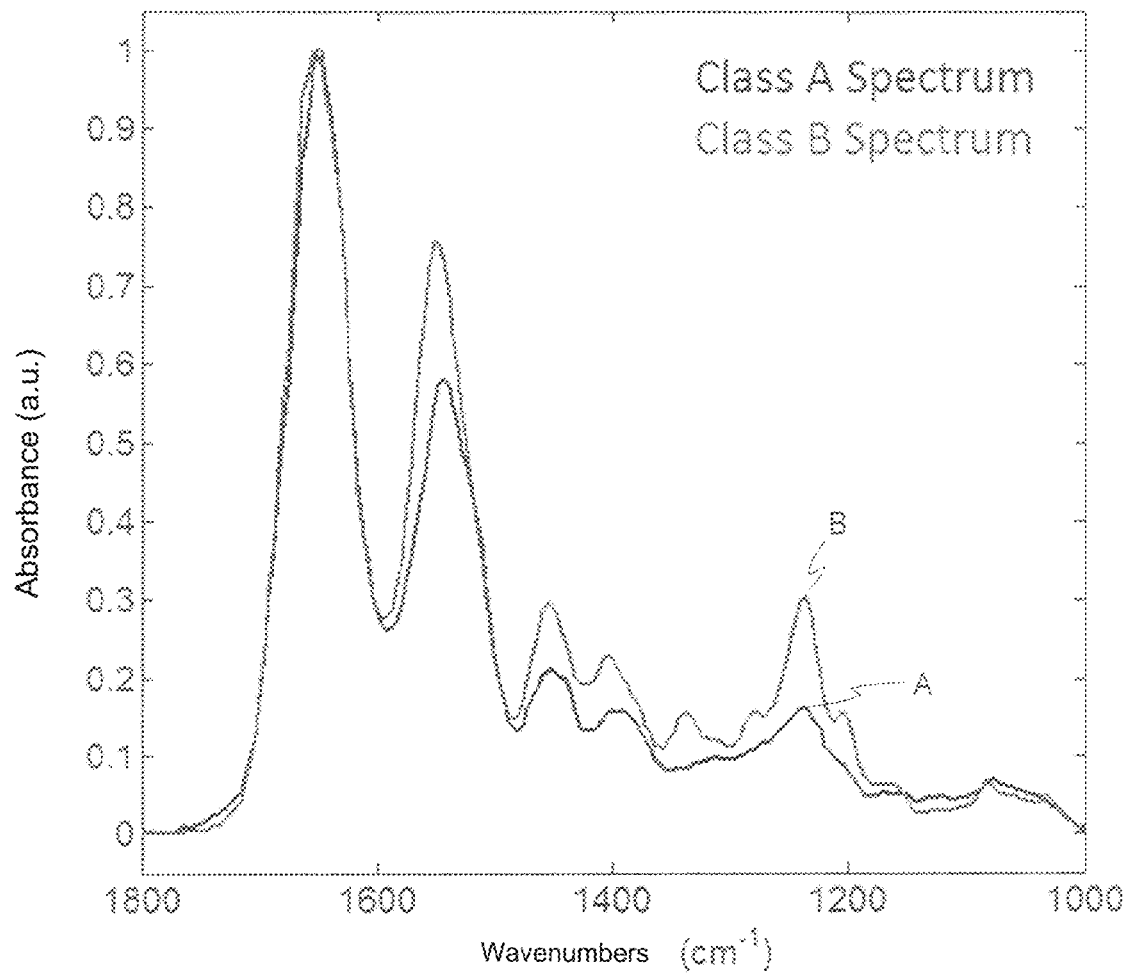
FIG. 6 is a graphical illustration of a normalized absorbance of a blood vessel wall sample and a human connective tissue sample in the mid-infrared spectral region of 1000-1800 $cm^{-1}$.

FIG. 6 is a graphical illustration of a normalized absorbance of a pair of training samples in differing classes, i.e. Class A and Class B, in the mid-infrared spectral region of 1000-1800 cm$^{-1}$. For example, FIG. 6 illustrates the mid-infrared spectra of two classes of human tissue, with Class A being recorded from a blood vessel wall sample, and Class B being recorded from a connective tissue sample. It should be noted that a number of visually discernible spectral differences are apparent between the different classes. Further, it should be noted that in certain embodiments, as provided herein, the wavelengths in which these discernible spectral differences occur can be used to quickly identify between a Class A sample and a Class B sample without requiring a full spectral analysis of the entire mid-infrared range.

With such design, the full spectral range of two known samples can be used to identify a plurality of diagnostic wavelengths that provide the most diagnostic spectral features as a means of distinguishing between these sample types. FIG. 6 illustrates one such diagnostic wavelength, e.g., approximately 8064.52 nanometers (wavenumber 1240 cm$^{-1}$), that could be used as a diagnostic spectral feature (gaps between the curves) between the samples. Once these diagnostic spectral features are learned between the different sample types, only the plurality of diagnostic wavelengths are needed to quickly identify subsequent possible samples as one or the other of these sample types.

Figure 7:
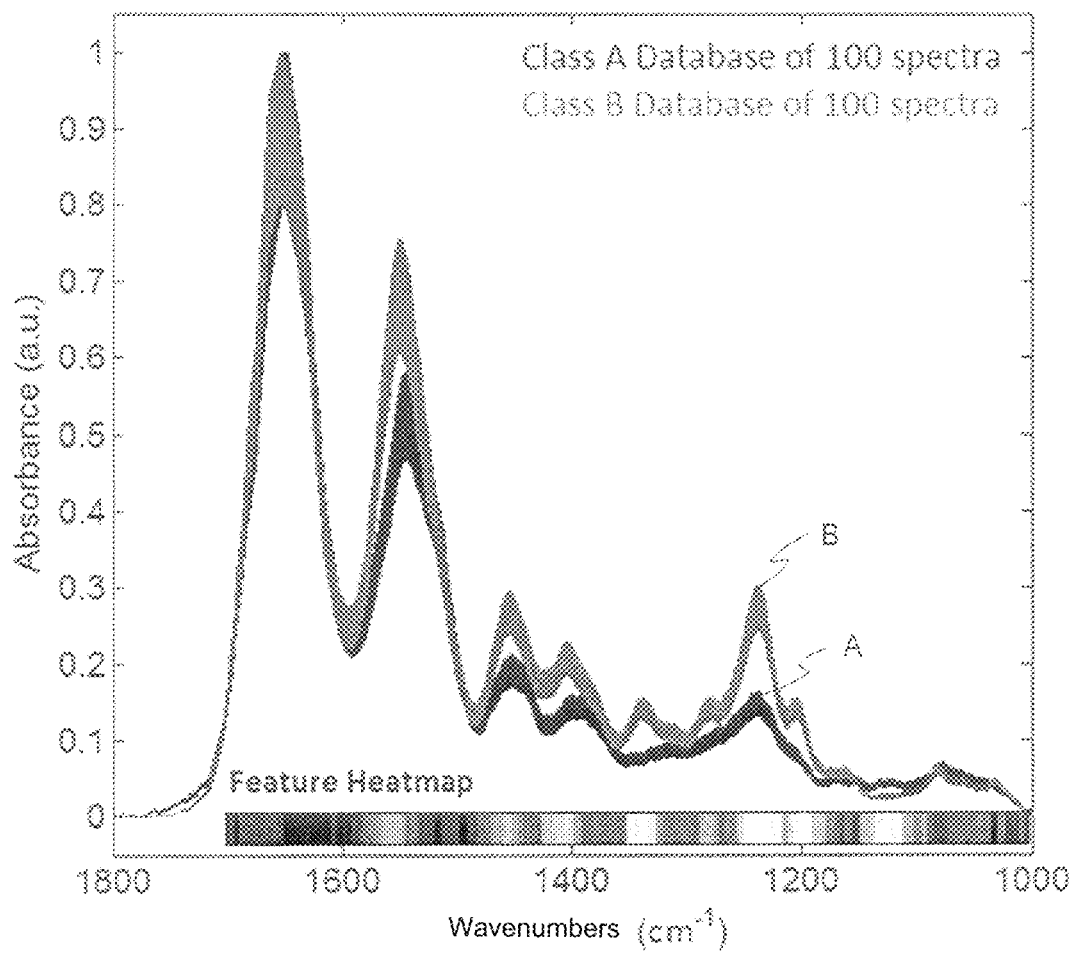
FIG. 7 is a graphical illustration showing absorbance for the mid-infrared spectral sets modeled from the samples graphically illustrated in FIG. 6.

FIG. 7 is a graphical illustration showing absorbance for the mid-infrared spectral sets modeled from the samples graphically illustrated in FIG. 6. In particular, FIG. 7 illustrates the mid-infrared spectral data sets modeled from Class A and Class B in FIG. 6. These data sets were generated by multiplying the spectra in FIG. 6 by a scaling factor (0.8-1.0 in 100 increments), rather than applying random variance with a set of criterion. These data sets were created to model relative changes in sample thickness of material, and thus path length travelled by the interrogating light.

In FIG. 7, the Class A data set includes one hundred spectra, and the Class B data set includes one hundred spectra. As provided herein, classification of different classes of a material is possible using mid-infrared spectroscopy when the intra-class variance is smaller than the inter-class variance. In this design, even with the spectral differences due to the factors associated with the model, the spectra break into two distinct classes (data sets) that can then be used to develop the heat map for determining a plurality of best wavelengths for classification. Again, as provided herein, the wavelengths in which these spectral differences occur can be used to quickly identify between a Class A sample and a Class B sample without spectral analysis of the entire mid-infrared range. By identification of diagnostic spectral features that provide the greatest discriminative power, supervised algorithms can be trained to robustly and accurately classify new challenge data.

FIG. 7 also includes a feature heat map that was calculated using the recorded wavelength absorbance values between wavenumbers 1000 and 1700 cm$^{-1}$ as spectral features and a statistical t-test. In the feature heat map, the colors range from black that describe a poor discriminant factor (i.e. with little or no variance between the classes), to white that describe a high discriminant factor (i.e. with relatively large variance between the classes). In this example, the highest discriminant factor is at approximately 8064.52 nanometers (wavenumber 1240 cm$^{-1}$) (illustrated with the white hue in the heat map). Thus, the wavelengths that correspond to the white areas (or lighter colored areas) of the feature heat map can be used to quickly identify between a Class A sample (i.e. a human blood vessel wall sample) and a Class B sample (i.e. a human connective tissue sample) without spectral analysis of the entire mid-infrared range.

Figure 8:
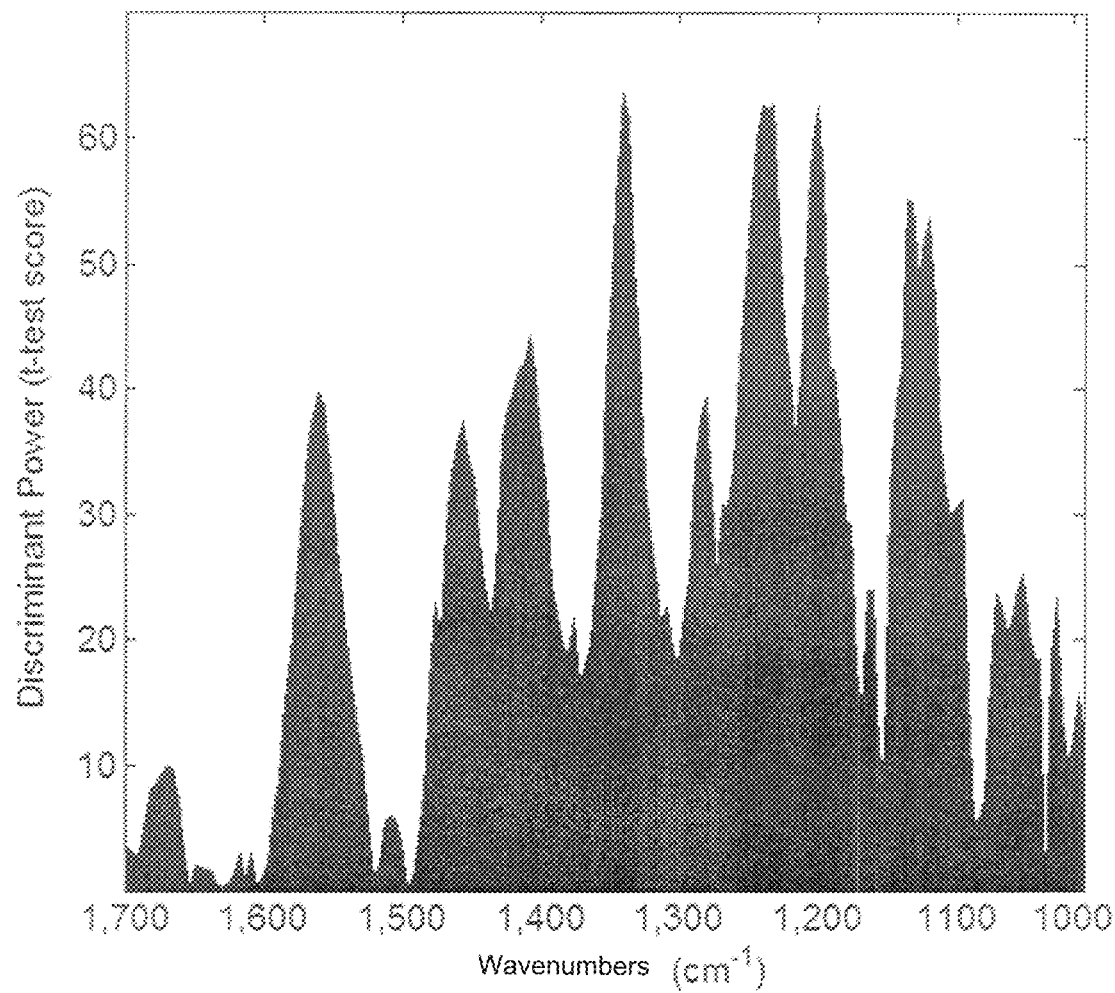
FIG. 8 is a graphical illustration showing discriminant power with an area plot created from t-test scores calculated for absorbance values in the spectral range of 1000-1700 $cm^{-1}$ for the data sets illustrated in FIG. 7.

FIG. 8 is a graphical illustration showing discriminant power with an area plot created from t-test scores calculated for absorbance values in the spectral range of wavenumbers 1000-1700 cm$^{-1}$ for the data sets (i.e. the Class A and Class B data sets) illustrated in FIG. 7. It should be appreciated that there are many methods and statistical tests that can be used to rank features. For example, as demonstrated in FIG. 8, calculated t-test scores were utilized. Simply stated, the two sample t-test is a parametric that compares the location parameter of two independent data samples.

Spectral features with the greatest discriminatory power can be observed at those wavelengths that provide the highest peaks in the diagram. Thus, the diagnostic wavelengths that correspond to the highest peaks in the diagram can be used to quickly identify between a Class A sample and a Class B sample without spectral analysis of the entire mid-infrared range.

Figure 9:
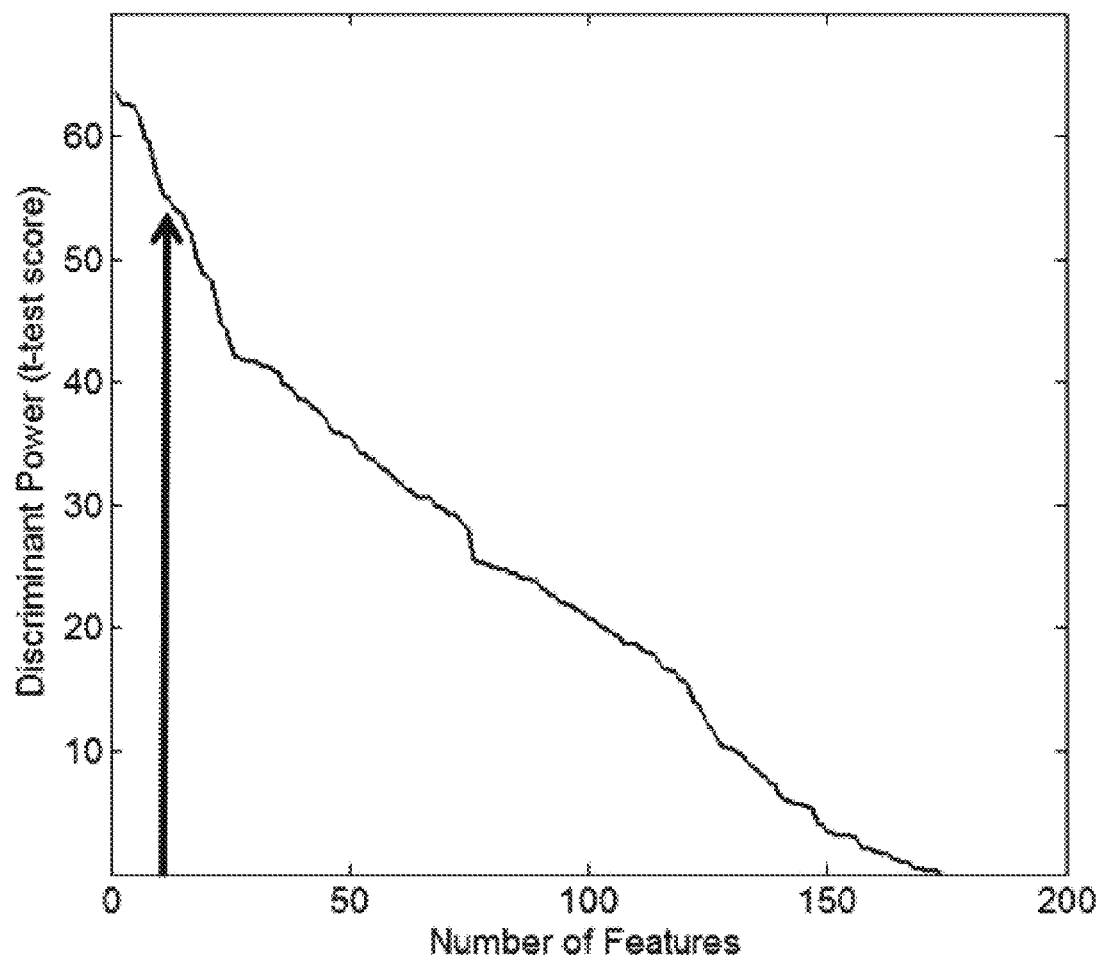
FIG. 9 is a graphical illustration showing discriminant power with a line plot created from reordered t-test scores calculated for absorbance values in the spectral range of 1000-1700 $cm^{-1}$ for the data sets illustrated in FIG. 7.

FIG. 9 is a graphical illustration showing discriminant power with a line plot created from reordered t-test scores calculated for absorbance values in the spectral range of 1000-1700 cm$^{-1}$ for the data sets (i.e. the Class A and Class B data sets) illustrated in FIG. 7. More specifically, the diagram in FIG. 9 was created by reordering the features from highest to lowest t-test score, so now the t-test score will decrease with increasing number of features.

A plot such as was created in FIG. 9 can be used to get a preliminary idea of how many diagnostic features could suffice to accurately classify an unknown sample, since plateaus or drops are again related to how well the features are able to segment the classes. This plot can help determine when significant drops in the t-test score are observed, and thus features below this point have a reduced ability to segment between the two classes.

The black arrow in the diagram indicates a potential cut-off point in the curve that describes a significantly reduced number of features that has the potential to accurately classify between the two groups of data. In certain embodiments, the wavelengths that correspond to the features on the left of the arrow can be used to quickly identify between a Class A sample and a Class B sample without spectral analysis of the entire mid-infrared range. Generally, the more information you have, the better the two classes may be classified. However, there will come a point when the useful information will plateau and the classification will cease to improve. This can be measured by creating individual classification algorithms for 1 to n (maximum number of inputs) features and reporting the algorithms accuracy to classify a plurality of unknown spectra, and reporting this as a line plot.

Further, as mentioned above, in certain embodiments, the unknown sample 10A (illustrated in FIG. 1A) can be prepared to improve the accuracy of the spectral analysis of the unknown sample 10A. For example, in such embodiments, it may be desired to prepare the unknown sample 10A such that the unknown sample 10A has a relatively large spatially homogeneous region 10B.

Samples can be prepared onto infrared amenable substrates using a variety of different methodologies, that include but are not limited to: (i) microtome sections of sample (solids); (ii) compression cell (solids, liquids, suspensions); (iii) spin deposition by centrifugation (suspensions and liquids); (iv) microliter droplets of sample (suspensions and liquids—hand pipette); and (v) nanoliter and picoliter droplets of sample (suspensions and liquids by robotic based instrumentation).

Figure 10:
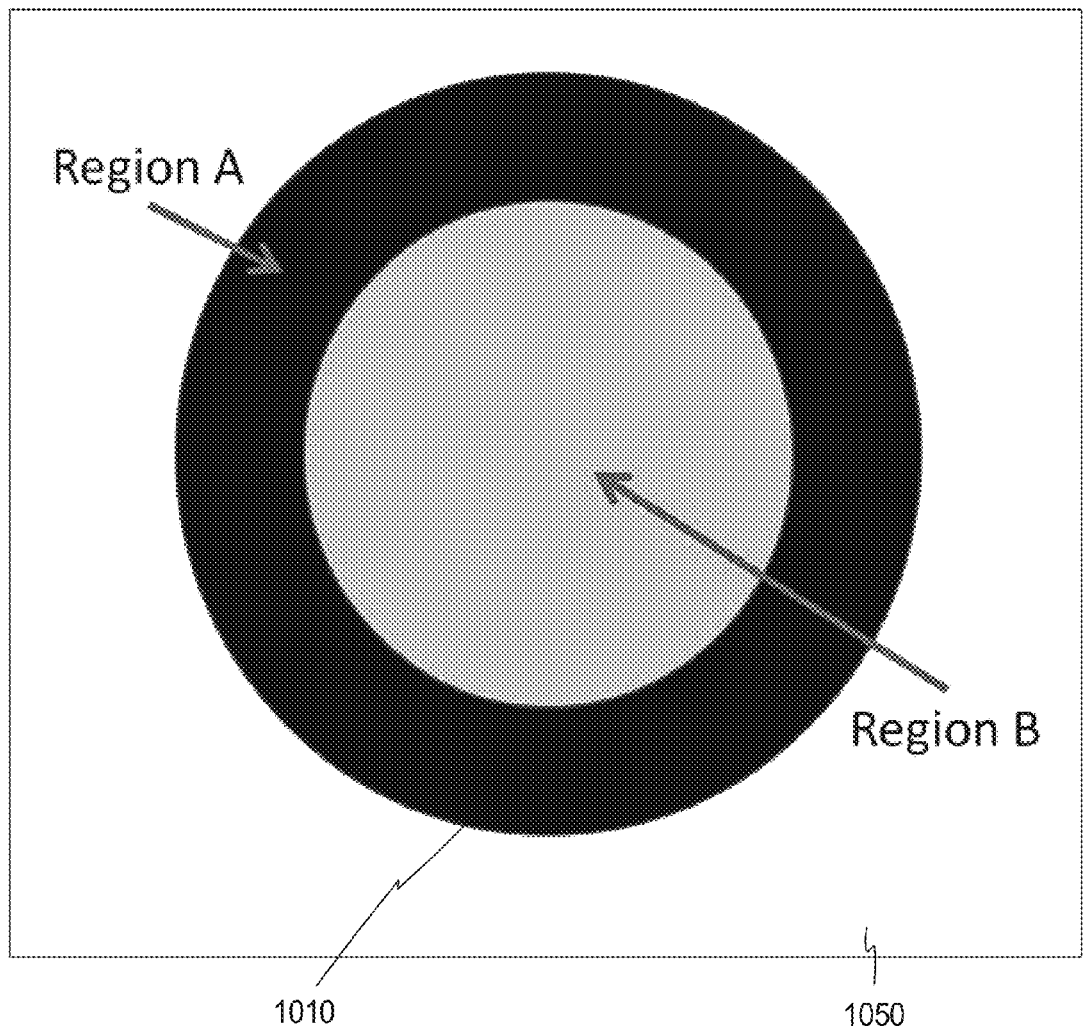
FIG. 10 is a graphical representation of a circular deposition of a sample onto an infrared amendable substrate.

FIG. 10 is a graphical representation of a circular deposition of a unknown sample 1010 onto an infrared amenable substrate 1050. Region A (black) illustrates areas on the deposit that describe recorded data that are not optimal for sample characterization or classification. The criterion for sub-optimal data can be characterized by a variety of constraints that include, but are not limited to, the measured absorbance of the material at any or all mid-infrared wavelengths, and the distortion of spectral features from scattering artifacts mediated by the sample or the substrate. Region B (grey) represents the areas on the deposit that are ideal for spectroscopic evaluation, characterization and classification.

In one non-exclusive embodiment, the unknown sample 1010 is prepared utilizing a handheld micro-pipette to create a circular film sample on the order of 1-2 mm in diameter using 0.5 µl of fluid. In this example, the unknown sample 1010 will have a relatively large Region "B" that is substantially homogeneous. Alternatively, the unknown sample 1010 can have a different size and/or shape than illustrated in FIG. 10, or can be prepared in a different fashion. For example, an automated machine can be used to deposit the unknown sample 1010 onto the substrate 1050.

As provided above, in FIG. 10, the dried unknown sample 1010 has a variable topology, with a thick ring "A" that is formed on the surrounding edges of the spot "B". Within this ring "A", the data collected is often compromised since the absorbance intensities are often outside the linear range of the detector response and show saturation. However, within the middle of the spot "B", a large area can be actively extracted for spectral analysis. Further, dried biofluids are relatively homogenous, and that in turn provides spectral data relatively free of adverse scattering. Spectral profiles show little if any baseline oscillation allowing robust classification algorithms to be constructed without rigorous scattering correction.

The measured spectra from samples can be altered or confounded by a number of sample or substrate mediated scattering effects, such as may be present within ring "A" illustrated in FIG. 10. These potential scattering effects include, but are not limited to: (i) mixing of absorptive and reflective line shapes; (ii) Mie scattering; (iii) resonant Mie (RMie) scattering; and (iv) optical standing wave artifact. As a consequence, the mid-infrared spatially resolved microscopic analysis of structurally heterogeneous samples, with complex morphological structures and refractive index mediated scattering artifacts, can be problematic for accurate sample classification and may require a vastly greater number of wavelengths to render a classification, or require computational correction and the measurement of a full or substantially sampled mid-infrared spectrum to effectively model spectral and baseline distortions.

Figure 11:
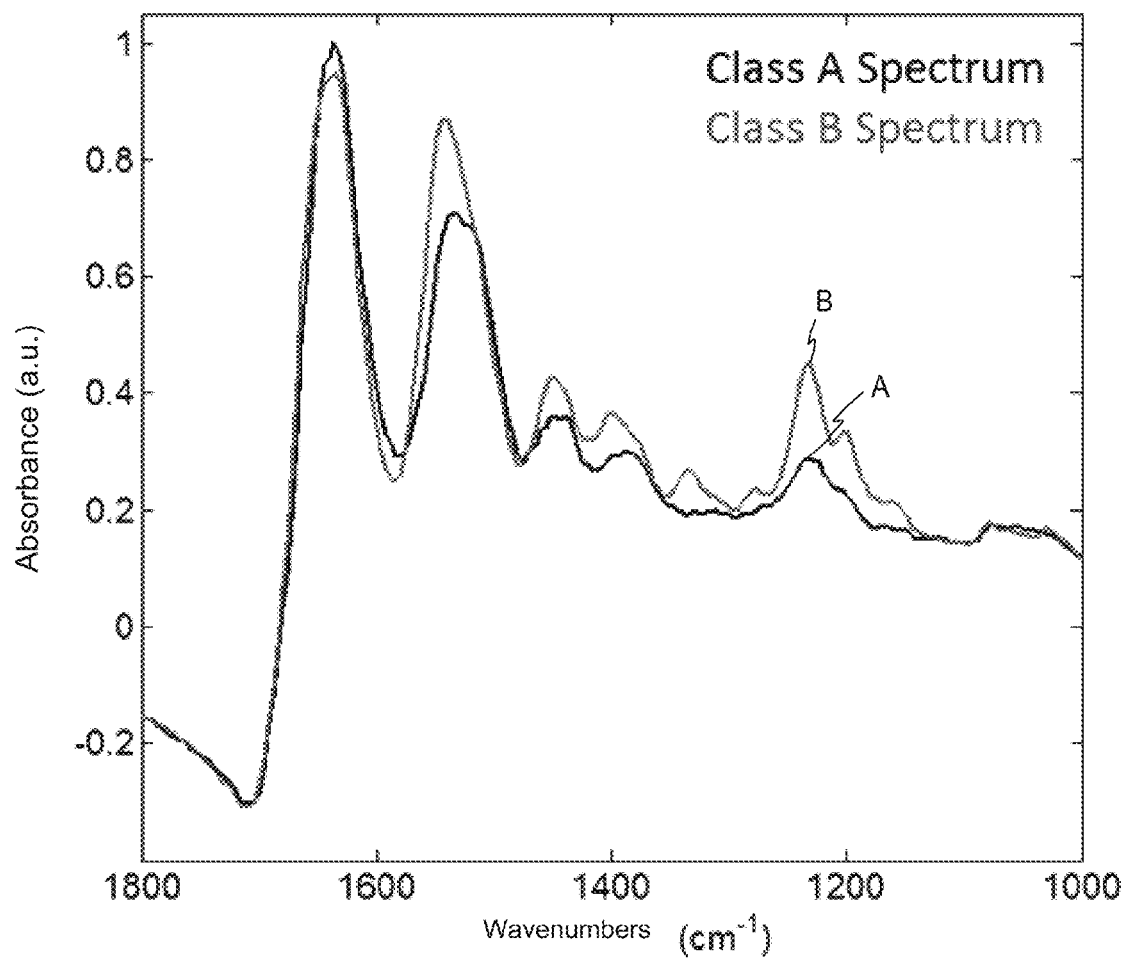
FIG. 11 is a graphical illustration of the mid-infrared spectrum of the human connective tissue sample and the blood vessel wall sample in the spectral region of 1000-1800 $cm^{-1}$ as shown in FIG. 6, with a mixing of reflective and absorptive line shapes.

FIG. 11 is a graphical illustration of the mid-infrared spectrum of the human connective tissue sample and the blood vessel wall sample in the spectral region of 1000-1800 cm$^{-1}$ as shown in FIG. 6, with a mixing of reflective and absorptive line shapes. The mixing of absorptive and reflective components distorts the spectral features such that changes in band intensities and band wavelengths are observed. As a consequence, the number of spectral features required to robustly partition the classes is increased. The mathematical relationship between absorptive and reflective band shapes can be provided by the Kramers-Kronig (KK) transformation.

However, in certain embodiments, as provided herein, the mid-infrared spatially resolved microscopic analysis of structurally homogenous samples (e.g., such as is shown in spot "B" in FIG. 10) is more trivial, since such scattering artifacts are not observed, or have a significantly reduced and manageable effect. Therefore, it is the ideal type of sample to exploit a methodology whereby only a small number of interrogation wavelengths are probed to render a classification.

Referring back to FIG. 10, a sample may compose spatial regions whereby the spectral data is not optimal, or describes a unique feature that is spatially orientated in a contiguous region. Mathematical algorithms can be constructed that partition sub-optimal pixels from further analysis. Algorithms may also be constructed to characterize and classify pixels within images that belong to different classes of sample morphology or chemistry.

The type of substrate 1050 utilized for retaining the unknown sample 10A10 can vary. For example, in some embodiments, the substrate 1050 can be made of $CaF_2$. Additionally, for transmission, in one non-exclusive example, the substrate 1050 can be made of zinc selenide, or ZnSe. Alternatively, other materials can be utilized for the substrate 1050, such as $BaF_2$, diamond, or Ge. In certain embodiments, the substrate 1050 is a mid-infrared amenable substrate with properties that allows interrogation of the unknown sample 10A10 using a transmission, transflection and reflection collection geometry.

Figure 12A:
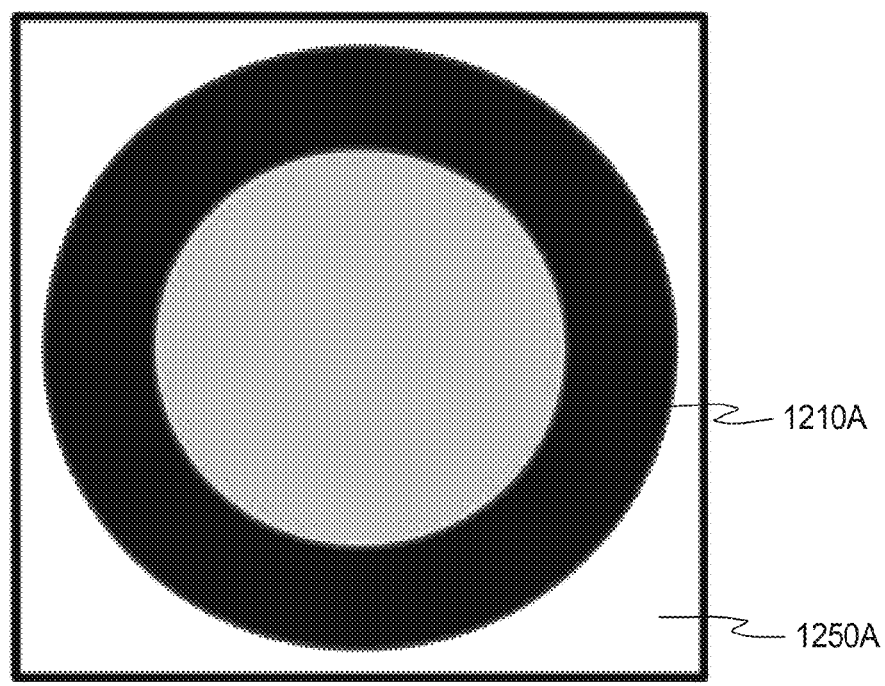
FIG. 12A is a graphical representation of a single sample deposit onto an infrared amenable substrate.

FIG. 12A is a graphical representation of a single sample 1210A deposited onto an infrared amenable substrate 1250A. In this embodiment, the single sample deposit 1210A is prepared, i.e. sized and shaped, to fit within a single frame of the light sensing device 26 (illustrated in FIG. 1A) of the analysis assembly 12 (illustrated in FIG. 1A).

Thus, the sample 1210A can be prepared so that a single sample deposit can be examined in a single frame of the light sensing device 26 of the analysis assembly 12. Conversely, preparation techniques can be adapted to enable multiple sample deposits to be examined in a single frame of the light sensing device 26 of the analysis assembly 12.

Figure 12B:
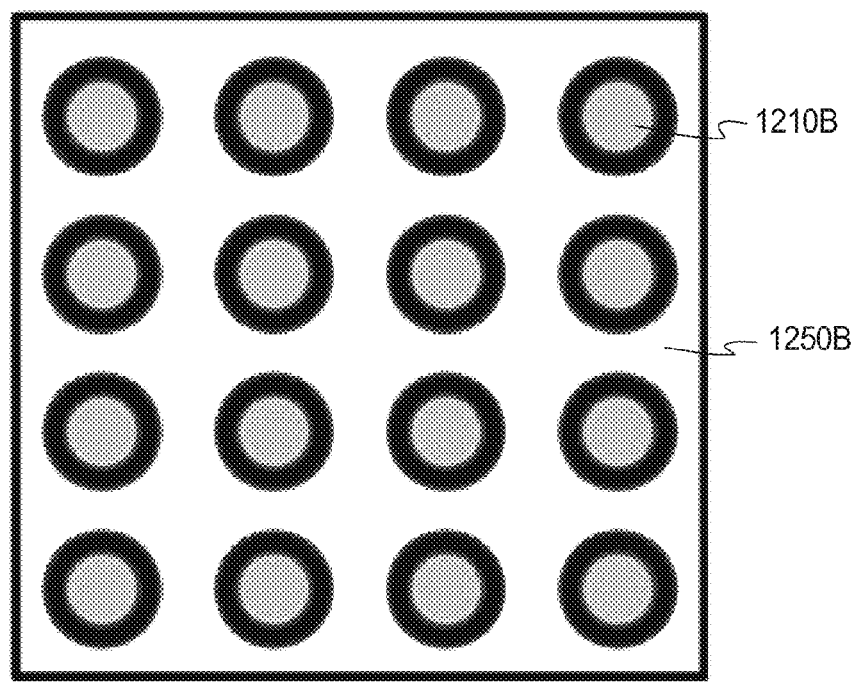
FIG. 12B is a graphical representation of a plurality of sample deposits onto an infrared amenable substrate.

FIG. 12B is a graphical representation of a plurality of sample deposits 1210B onto an infrared amenable substrate 1250B. In this example, multiple sample deposits 1210B are prepared to fit within a single frame of the light sensing device 26 (illustrated in FIG. 1A) of the analysis assembly 12 (illustrated in FIG. 1A). It should be noted that the number, arrangement, and size of the samples 1210B can be different than that illustrated in FIG. 12B.

Figure 13A:
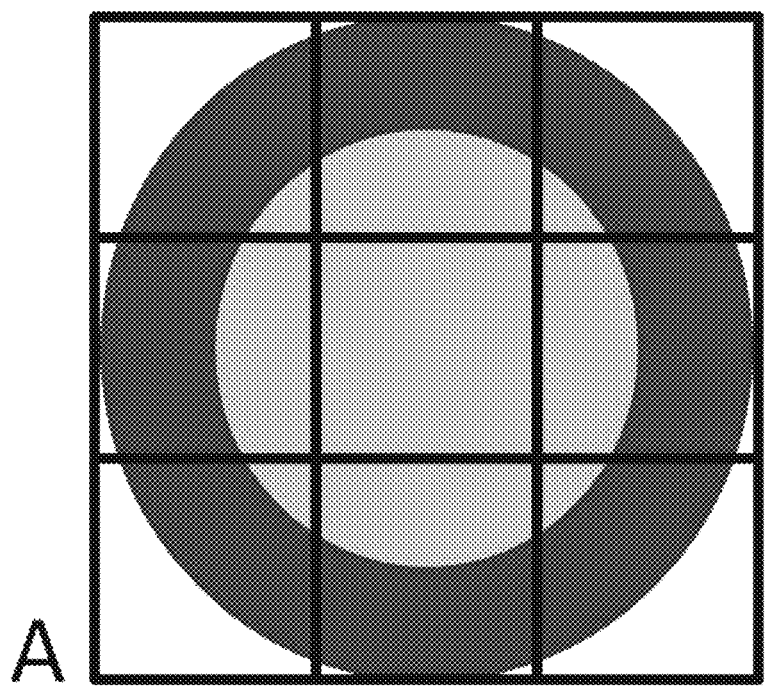
FIG. 13A is a simplified schematic illustration of a plurality of images of a single sample, when the single sample is larger than a single image that is captured by an imaging device.

FIG. 13A is a simplified schematic illustration of a plurality of images of a single sample. More particularly, FIG. 13A illustrates the situation when the sample is larger than a single image that is captured by the light sensing device 26 (illustrated in FIG. 1A) of the analysis assembly 12 (illustrated in FIG. 1A). In this embodiment, the sample can be analyzed with multiple images and the multiple images can be joined together for analysis of the sample.

Figure 13B:
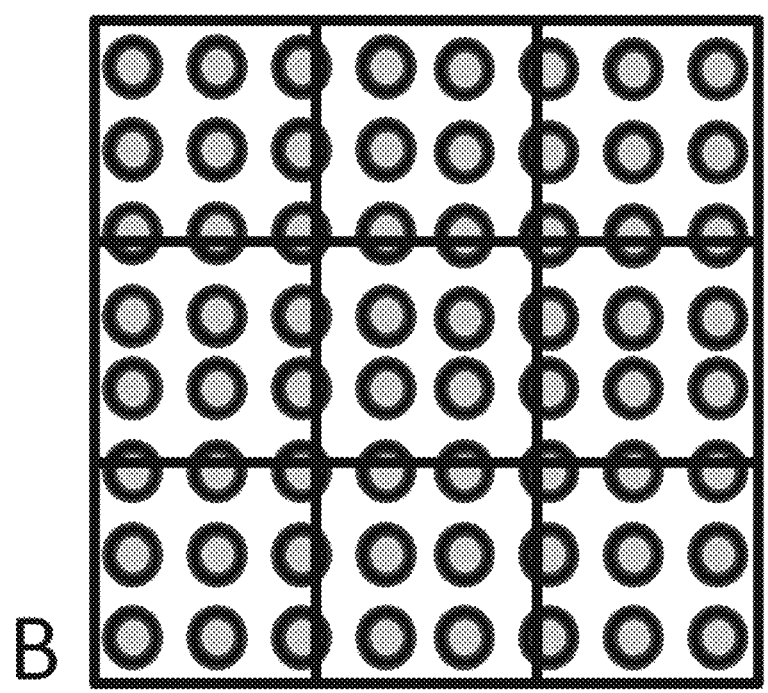
FIG. 13B is a simplified schematic illustration of a plurality of images of a plurality of samples, when the plurality of samples are larger than a single image that is captured by an imaging device.

FIG. 13B is a simplified schematic illustration of a plurality of images of a plurality of samples. More particularly, FIG. 13B illustrates the situation when multiple samples are larger than a single image that is captured by the light sensing device 26 (illustrated in FIG. 1A) of the analysis assembly 12 (illustrated in FIG. 1A). In this embodiment, the multiple samples can be analyzed with multiple images and the multiple images can be joined together for analysis of the samples.

Figure 14:
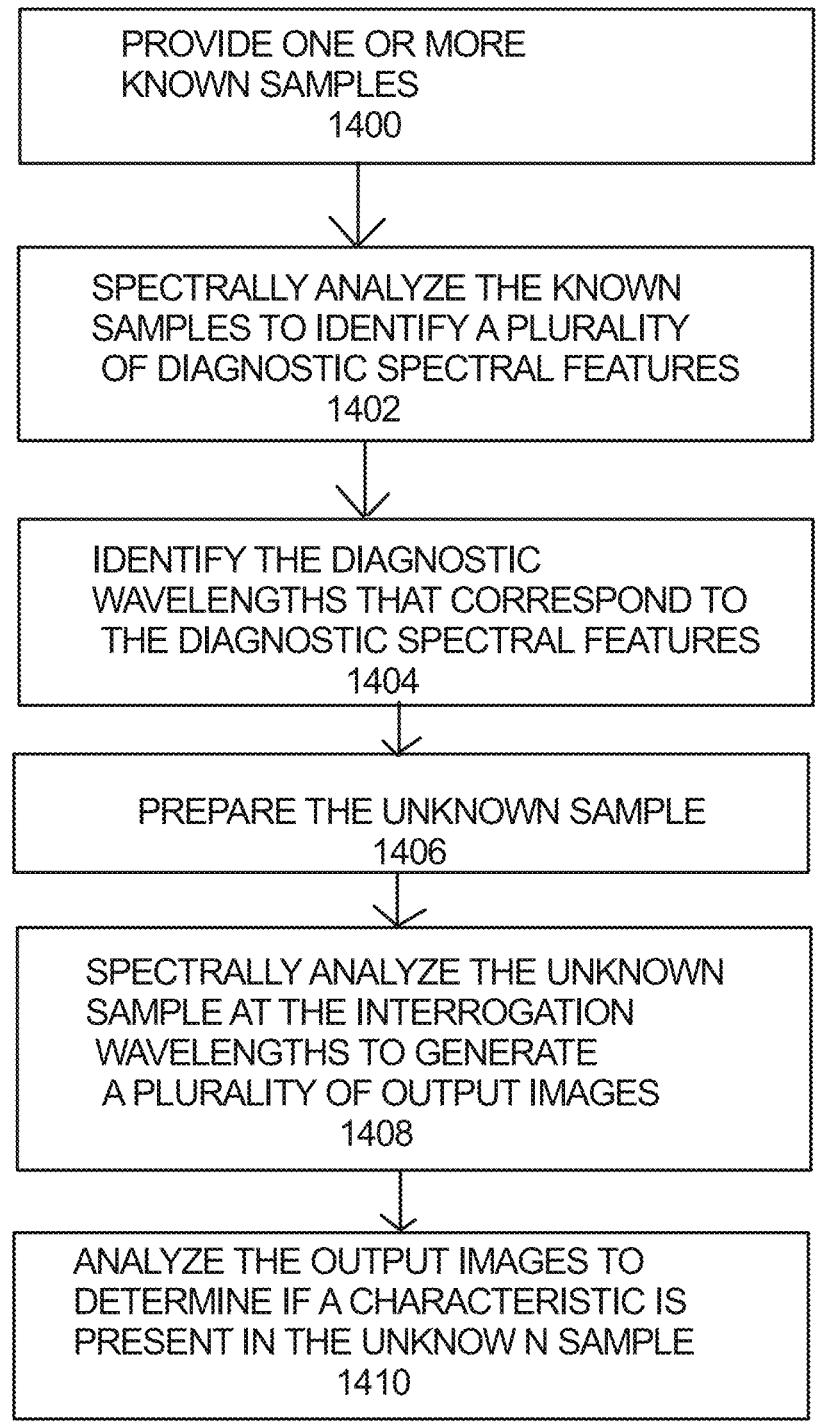
FIG. 14 is a simplified illustration of a flow chart that outlines a method having features of the present invention.

FIG. 14 is a flow chart that illustrates one method having features of the present invention. In this embodiment, at block 1400, one or more known samples are provided for examination. Next, at block 1402, each known sample is spectrally analyzed at a plurality (e.g. hundreds or thousands) of alternative wavelengths in the mid-infrared spectrum and a limited number of diagnostic spectral features are identified. Subsequently, at block 1404, the diagnostic wavelengths that correspond to the diagnostic spectral features are identified.

Next, at block 1406, the unknown sample is prepared. Subsequently, at block 1408, the unknown sample is spectrally analyzed at each of the interrogation wavelengths to generate a separate output image for each interrogation wavelength. Finally, at block 1410, the output images are analyzed to determine if a characteristic is present in the unknown sample.

It is understood that although a number of different embodiments of the analysis assembly 12 have been illustrated and described herein, one or more features of any one embodiment can be combined with one or more features of one or more of the other embodiment, provided that such combination satisfies the intent of the present invention. Additionally, it will be obvious to those recently skilled in the art that modifications to the analysis assembly 12 and methods of manufacture disclosed herein may occur, including substitution of various component values or modes of connection, without departing from the true spirit and scope of the disclosure.

While a number of exemplary aspects and embodiments of an analysis assembly 12 have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A method for spectrally analyzing an unknown sample for the existence of a characteristic, the method comprising:
   analyzing a known sample having the characteristic to identify a plurality of diagnostic spectral features, each diagnostic spectral feature being present at a different diagnostic wavelength that is in a mid-infrared spectral region;
   providing a spatially homogeneous region of the unknown sample;
   directing a plurality of interrogation beams at the spatially homogeneous region with a laser source, each of the interrogation beams being nominally monochromatic and having a different interrogation wavelength;
   wherein each interrogation wavelength corresponds to a different one of the diagnostic wavelengths;
   acquiring a plurality of separate output images of the unknown sample with an image sensor that senses light in the mid-infrared spectral region, wherein each of the output images is acquired while the unknown sample is illuminated by a different one of the interrogation beams;
   and analyzing less than fifty output images to analyze whether the characteristic is present in the unknown sample with a control system that includes a processor;
   wherein the spatially homogeneous region of the unknown sample is substantially structurally homogeneous so that the interrogation wavelengths of the spectral features have shifted less than 10 $cm^{-1}$ than expected when directed at the spatially homogeneous region.

2. The method of claim 1 wherein analyzing less than fifty output images includes analyzing less than thirty output images to analyze whether the characteristic is present in the unknown sample with the control system.

3. The method of claim 1 wherein analyzing less than fifty output images includes analyzing less than twenty output images to analyze whether the characteristic is present in the unknown sample with the control system.

4. The method of claim 1 wherein analyzing a known sample includes identifying less than fifty diagnostic spectral features.

5. The method of claim 1 wherein analyzing a known sample includes identifying less than thirty diagnostic spectral features.

6. The method of claim 1 wherein acquiring a plurality of separate output images includes capturing a plurality of separate preliminary images for each interrogation beam, and using the separate preliminary images to determine the separate output image for each interrogation beam.

7. The method of claim 1 wherein acquiring a separate output image includes modulating the wavelength of each interrogation beam while capturing the corresponding output image.

* * * * *